(12) United States Patent
Danso-Danquah et al.

(10) Patent No.: US 7,601,739 B2
(45) Date of Patent: Oct. 13, 2009

(54) COMPOUNDS HAVING ANTIESTROGENIC AND TISSUE SELECTIVE ESTROGENIC PROPERTIES, AND COMPOUNDS WITH ANTI-ANDROGENIC PROPERTIES FOR TREATMENT OF PROSTATE CANCER AND ANDROGEN RECEPTOR DEPENDENT DISEASES

(75) Inventors: Richmond Danso-Danquah, Richmond, VA (US); Donald J. Abraham, Richmond, VA (US); Hsiang-Ru Lin, Taipei (TW); Jim Christian Burnett, Richmond, VA (US)

(73) Assignee: Virgina Commonwealth University, Richmond, VA (US)

( * ) Notice: Subject to any disclaimer, the term of this patent is extended or adjusted under 35 U.S.C. 154(b) by 575 days.

(21) Appl. No.: 11/349,339

(22) Filed: Feb. 8, 2006

(65) Prior Publication Data
US 2006/0287359 A1 Dec. 21, 2006

(51) Int. Cl.
*C07D 217/00* (2006.01)
*A61K 31/47* (2006.01)
(52) U.S. Cl. .......................... 514/307; 546/146; 546/149
(58) Field of Classification Search ....................... None
See application file for complete search history.

(56) References Cited

FOREIGN PATENT DOCUMENTS

| WO | WO 9415959 | 7/1994 |
|---|---|---|
| WO | WO 95/35316 | 12/1995 |

*Primary Examiner*—Zinna N Davis
(74) *Attorney, Agent, or Firm*—Whitham Curtis Christofferson & Cook, PC

(57) ABSTRACT

Compounds for the treatment of estrogen-receptor related maladies are provided. Compounds with anti-androgenic properties also are provided. In particular, the invention provides compounds that are tetrahydroquinoline phenylamide derivatives and are useful for the treatment of breast and prostate cancer, and osteoporosis.

26 Claims, 12 Drawing Sheets

| Compound | n | $R_1$* | Relative Binding Affinity |
|---|---|---|---|
| 1a | 0 | 2', 3' -CH$_3$ | 6.8 |
| 1b | 0 | 3', 5' -CH$_3$ | 6.4 |
| 1c | 0 | 3', 5' -F | 3.9 |
| 1d | 0 | 3' -F, 2'-CH$_3$ | 2.9 |
| 1e | 0 | 3' -F, 4'-CH$_3$ | 5.1 |
| 1f | 0 | 3' -OH, 4'-CH$_3$ | 2.3 |
| 1g | 0 | 3', 4'-OH | 6.8 |
| 1h | 0 | 4'- CH$_2$ -(CF$_3$)$_2$(OH) | 12.6 |
| 2a | 1 | 3', 5' -CF$_3$ | 6.4 |
| 2b | 1 | 3' -F, 4'-OH | 13.4 |
| Flutamide | | | 1 |
| CPA | | | 150 |

COMPOUNDS HAVING ANTIESTROGENIC AND TISSUE SELECTIVE ESTROGENIC PROPERTIES, AND COMPOUNDS WITH ANTI-ANDROGENIC PROPERTIES FOR TREATMENT OF PROSTATE CANCER AND ANDROGEN RECEPTOR DEPENDENT DISEASES

This application claims priority to International patent application PCT/US2004/025186 (filed Aug. 6, 2004) of which it is a continuation-in-part, and to U.S. provisional Nos. 60/493,363 (filed Aug. 8, 2003) and 60/654,479 (filed Feb. 22, 2005).

The entire contents of each application to which priority is claimed is hereby incorporated by reference.

FIELD OF THE INVENTION

The invention generally relates to compounds that are useful for the treatment of estrogen-receptor related maladies. In particular, the invention provides tetrahydroquinoline phenylamide derivatives that are useful for the treatment of breast and prostate cancer, and osteoporosis. The invention also relates to compounds with anti-androgenic properties that are useful for the treatment of prostate cancer and androgen receptor dependent diseases.

BACKGROUND OF THE INVENTION

It is commonly acknowledged that estrogen and the estrogen receptors (ERs) play essential roles in the development of breast tumors, although the precise mechanisms involved have not been determined. Several treatment regimens for breast cancer have been developed that utilize Selective Estrogen Receptors Modulators (SERMs). Tamoxifen, a "first generation" SERM, (FIG. 7A) was developed more than 30 years ago and was approved by the Food and Drug Administration in 1985 for the treatment of breast cancers.

Tamoxifen antagonizes or mimics the effect of estrogen in a variety of tissues. For example, tamoxifen acts as an anti-estrogen in breast tissues and CNS system, and exerts estrogenic effects in bone, cardiovascular and endometrium tissues. In bone system, it initially was suspected that tamoxifen's antiestrogenic effects might accelerate bone resorption and increase the risk of developing osteoporosis. However, in vitro and in vivo studies have demonstrated that tamoxifen performs as an estrogen in bone, promoting maintenance of bone density, and is thus useful in the treatment of osteoporosis.

Although tamoxifen shows some beneficial estrogenic effects, it also has been proposed to promote uterus and liver carcinogenesis. Some tumors become resistant to treatment with tamoxifen over time. Only a few tamoxifen alternatives have been developed, e.g. Toremifene, GW 5638 and Idoxifene, and second generation SERMs such as Raloxifene, which is currently in clinical trials. Unfortunately, it appears that raloxifene may display cross-resistance to tamoxifen resistant tumors.

Estrogen receptors also play a role in prostate cancer, and in the development of osteoporosis. Thus, agents that modulate estrogen-receptors may also be useful for the treatment of those diseases.

There is thus an ongoing need to develop new compounds for the treatment of diseases related to estrogen receptor function, in particular for the treatment of breast and prostate cancer, and osteoporosis. This need is particularly acute in light of the tendency of tumors to become resistant to treatment with therapeutic agents after extended use, and in view of the desirability of discovering compounds with reduced deleterious side effects than those exhibited by currently known compounds.

SUMMARY OF THE INVENTION

The invention provides a series of compounds possessing antiestrogenic and tissue-selective estrogenic properties. The compounds may be used in the treatment of estrogen receptor related diseases, including breast and prostate cancer, and osteoporosis.

It is an object of the present invention to provide a compound of generic formula

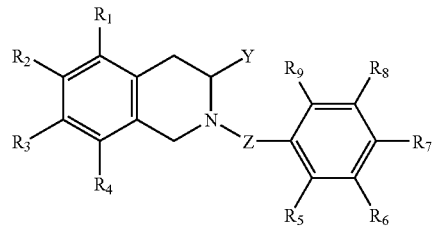

wherein
Z is selected from the group consisting of CO, $CH_2$, and $CO(CH_2)n$, where n=1 or 2;

R1, R2, R3, R4, R5, R6, R7, R8 and R9 are the same or different, and are selected from the group consisting of H, OH, halogens, R and OR, where R is a substituted or unsubstituted alkyl group having 1-4 carbons;

Y is selected from the group consisting of —$CH_2$—O—R10 and —$CH_2$—NH—R10; and R10 is selected from the group consisting of:

a) —$(CH_2)n$-C(═O)—N—R11, R12, where n=1-10 and R11 and R12 are the same or different, and are selected from the group consisting of substituted and unsubstituted $C_1$-$C_9$ alkyl, substituted and unsubstituted cycloalkyl, and substituted and unsubstituted aryl;

b) —$(CH_2)n$-S(═O)—N—R11, R12, where n=1-10 and R11 and R12 are the same or different, and are selected from the group consisting of substituted and unsubstituted $C_1$-$C_9$ alkyl, substituted and unsubstituted cycloalkyl, and substituted and unsubstituted aryl;

c) —$(CH_2)n$-$SO_2$—N—R11, R12, where n=1-10 and R11 and R12 are the same or different, and are selected from the group consisting of substituted and unsubstituted $C_1$-$C_9$ alkyl, substituted and unsubstituted cycloalkyl, and substituted and unsubstituted aryl;

d) —$(CH_2)n$-S(═O)—R11, where n=1-10 and R11 is selected from: substituted and unsubstituted $C_1$-$C_9$ alkyl, substituted and unsubstituted cycloalkyl, and substituted and unsubstituted aryl; and e) —$(CH_2)n$-$SO_2$—R11, where n=1-10 and R11 is selected from the group consisting of substituted and unsubstituted $C_1$-$C_9$ alkyl, substituted and unsubstituted cycloalkyl, and substituted and unsubstituted aryl.

In a preferred embodiment of the invention, the substituted and unsubstituted $C_1$-$C_9$ alkyl is —$CH_2CH_2CH_2CF_2CF_3$. In other preferred embodiments, R1, R2, R3, R4, R5, R6, R7, R8 and R9 are F, $OCH_3$, OH, $CH_3$ or Cl.

It is a further object of the invention to provide compounds with the following formulas:

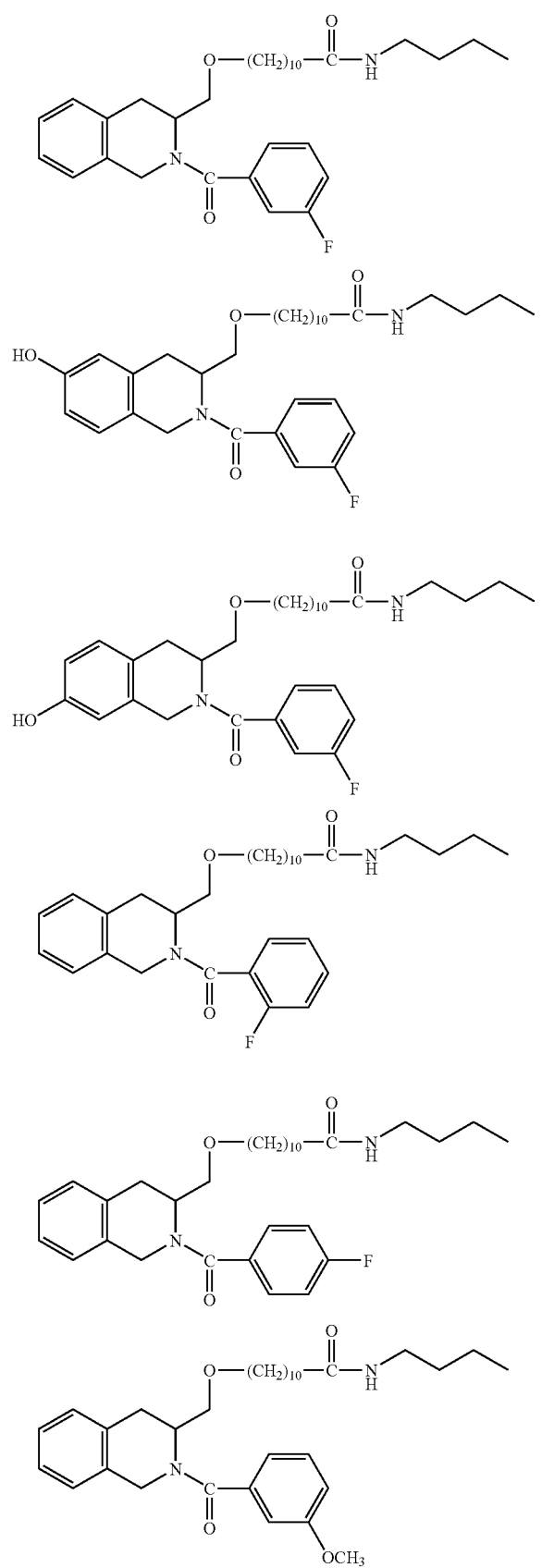
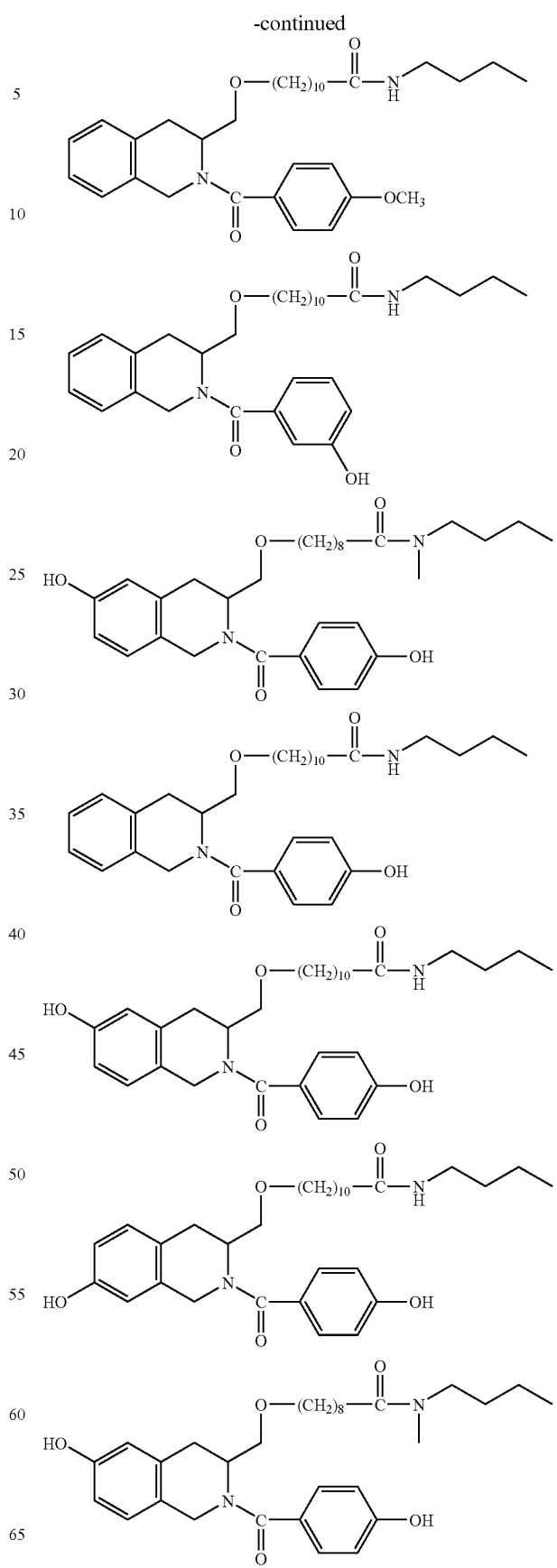

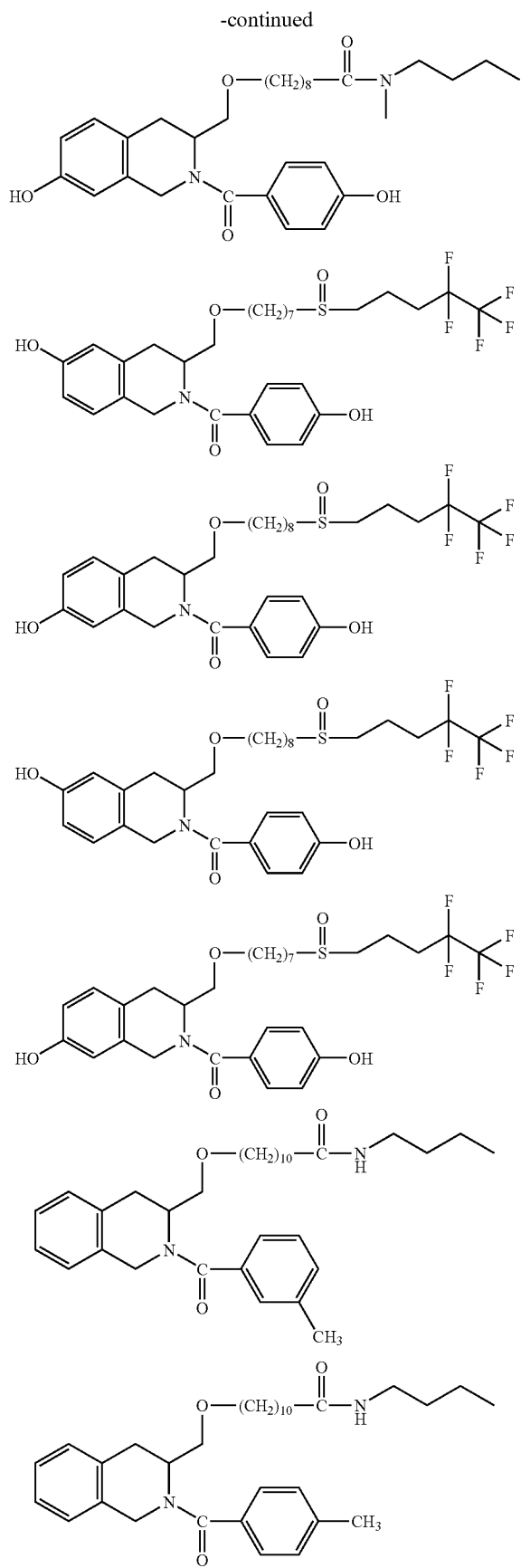

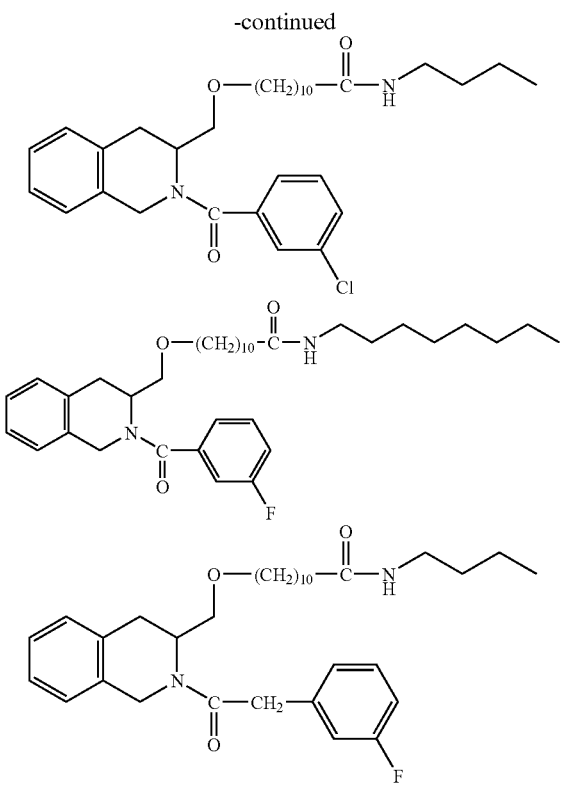

The invention further provides a method of inhibiting binding of estrogen in vivo or in vitro by providing a compound which binds to an estrogen binding site. The compound has the generic formula

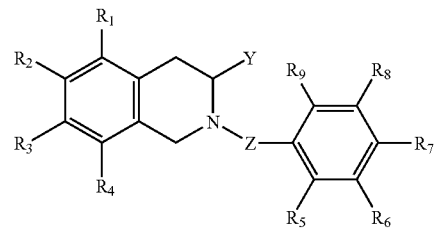

wherein

Z is selected from the group consisting of CO, $CH_2$, and $CO(CH_2)n$, where n=1 or 2;

$R_1$, $R_2$, $R_3$, $R_4$, $R_5$, $R_6$, $R_7$, $R_8$ and $R_9$ are the same or different, and are selected from the group consisting of H, OH, halogens, R and OR, where R is a substituted or unsubstituted alkyl group having 1-4 carbons;

Y is selected from the group consisting of —$CH_2$—O—$R10$ and —$CH_2$—NH—$R10$; and R10 is selected from the group consisting of:

a) —$(CH_2)n$-C(=O)—N—R11, R12, where n=1-10 and R11 and R12 are the same or different, and are selected from the group consisting of substituted and unsubstituted $C_1$-$C_9$ alkyl, substituted and unsubstituted cycloalkyl, and substituted and unsubstituted aryl;

b) —$(CH_2)n$-S(=O)—N—R11, R12, where n=1-10 and R11 and R12 are the same or different, and are selected from the group consisting of substituted and unsubstituted $C_1$-$C_9$ alkyl, substituted and unsubstituted cycloalkyl, and substituted and unsubstituted aryl;
c) —($CH_2$)n-$SO_2$—N—R11, R12, where n=1-10 and R11 and R12 are the same or different, and are selected from the group consisting of substituted and unsubstituted $C_1$-$C_9$ alkyl, substituted and unsubstituted cycloalkyl, and substituted and unsubstituted aryl;
d) —($CH_2$)n-S(—O)—R11, where n=1-10 and R11 is selected from: substituted and unsubstituted $C_1$-$C_9$ alkyl, substituted and unsubstituted cycloalkyl, and substituted and unsubstituted aryl; and
e) —($CH_2$)n-$SO_2$—R11, where n=1-10 and R11 is selected from the group consisting of substituted and unsubstituted $C_1$-$C_9$ alkyl, substituted and unsubstituted cycloalkyl, and substituted and unsubstituted aryl.

In a preferred embodiment of the invention, the substituted and unsubstituted $C_1$-$C_9$ alkyl is —$CH_2CH_2CH_2CF_2CF_3$. In other preferred embodiments, R1, R2, R3, R4, R5, R6, R7, R8 and R9 are F, $OCH_3$, OH, $CH_3$ or Cl.

In preferred embodiments of the method, the compound is

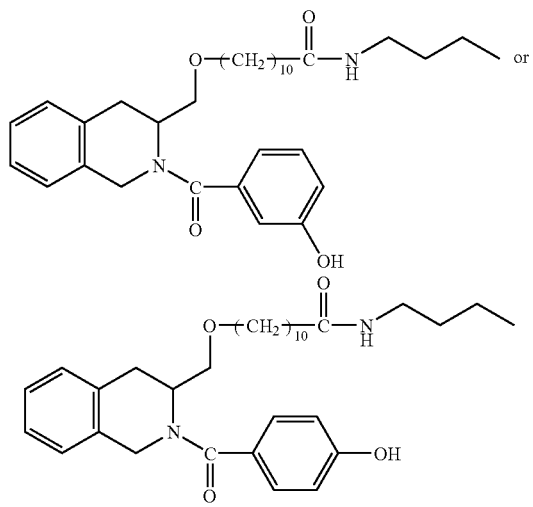

or

The invention further provides a method for treating tamoxifen-resistant breast cancer tumors in a patient in need thereof. The method comprises the step of administering to the patient a compound of generic formula

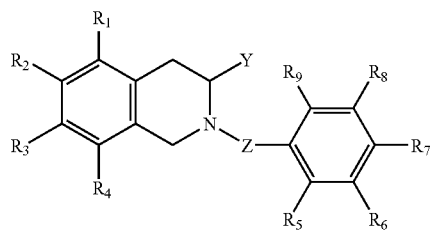

wherein

Z is selected from the group consisting of CO, $CH_2$, and CO($CH_2$)n, where n=1 or 2;

R1, R2, R3, R4, R5, R6, R7, R8 and R9 are the same or different, and are selected from the group consisting of H, OH, halogens, R and OR, where R is a substituted or unsubstituted alkyl group having 1-4 carbons;

Y is selected from the group consisting of —$CH_2$—O—R10 and —$CH_2$—NH—R10; and R10 is selected from the group consisting of:
a) —($CH_2$)n-C(=O)—N—R11, R12, where n=1-10 and R11 and R12 are the same or different, and are selected from the group consisting of substituted and unsubstituted $C_1$-$C_9$ alkyl, substituted and unsubstituted cycloalkyl, and substituted and unsubstituted aryl;
b) —($CH_2$)n-S(=O)—N—R11, R12, where n=1-10 and R11 and R12 are the same or different, and are selected from the group consisting of substituted and unsubstituted $C_1$-$C_9$ alkyl, substituted and unsubstituted cycloalkyl, and substituted and unsubstituted aryl;
c) —($CH_2$)n-$SO_2$—N—R11, R12, where n=1-10 and R11 and R12 are the same or different, and are selected from the group consisting of substituted and unsubstituted $C_1$-$C_9$ alkyl, substituted and unsubstituted cycloalkyl, and substituted and unsubstituted aryl;
d) —($CH_2$)n-S(=O)—R11, where n=1-10 and R11 is selected from: substituted and unsubstituted $C_1$-$C_9$ alkyl, substituted and unsubstituted cycloalkyl, and substituted and unsubstituted aryl; and
e) —($CH_2$)n-$SO_2$—R11, where n=1-10 and R11 is selected from the group consisting of substituted and unsubstituted $C_1$-$C_9$ alkyl, substituted and unsubstituted cycloalkyl, and substituted and unsubstituted aryl.

In another preferred embodiment, the invention provides compounds of the following formulae (A-1), (A-2), (A-3) and (A-4):

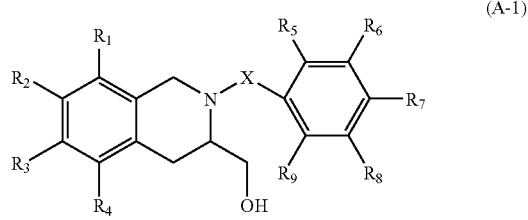

(A-1)

wherein in formula (A-1):

X is selected from the group consisting of CO, $CH_2$, and CO($CH_2$)n where n=1 or 2;

R1, R2, R3, R4, R5, R6, R7, R8 and R9 are the same or different, and are selected from: H; F; Br; Cl; $CF_3$; CN; $NO_2$; $CH_3$; OH; $OCH_3$; $OCF_3$; $NH_2$; $N(CH_3)_2$; $COOCH_3$ and COOH;

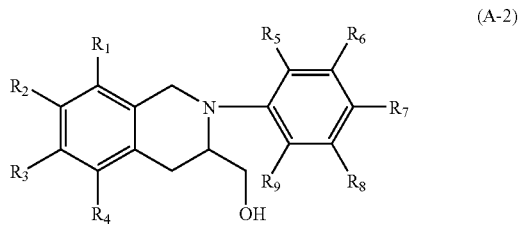

(A-2)

wherein in formula (A-2):

R1, R2, R3, R4, R5, R6, R7, R8 and R9 are the same or different, and are selected from: H; F; Br; Cl; $CF_3$; CN; $NO_2$; $CH_3$; OH; $OCH_3$; $OCF_3$; $NH_2$; $N(CH_3)_2$; $COOCH_3$ and COOH;

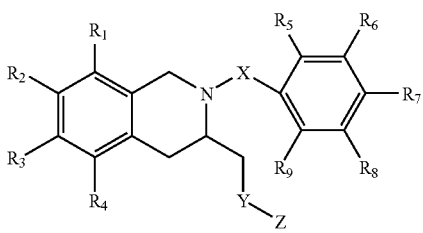

wherein in formulae (A-3):
Z is:

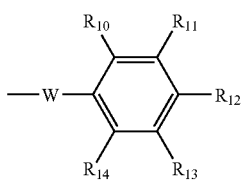

in which W is $(CH_2)_n$ (n=0 to 3); $SO_2$ or CO;

X is selected from the group consisting of CO, $CH_2$, and $CO(CH_2)n$ where n=1 or 2;

Y is selected from O or NH;

R1, R2, R3, R4, R5, R6, R7, R8 and R9 are the same or different, and are selected from: H; F; Br; Cl; $CF_3$; CN; $NO_2$; $CH_3$; OH; $OCH_3$; $OCF_3$; $NH_2$; $N(CH_3)_2$; $COOCH_3$ and COOH;

R10, R11, R12, R13 and R14 are the same or different, and are selected from H; F; Br; Cl; $CF_3$; CN; $NO_2$; $CH_3$;OH; $OCH_3$; $OCF_3$; $NH_2$; $N(CH_3)_2$; $COOCH_3$; COOH;

$(CH_2)_m CON(CH_3)_2$ (m=0 to 6) and $(CH_2)_m CON(CH_2 CH_3)_2$ (m=0 to 6);

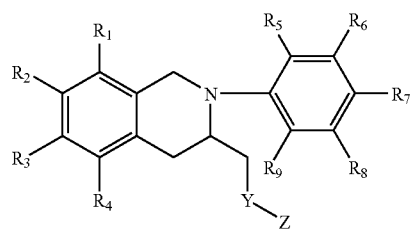

wherein in formula (A-4):
Z is

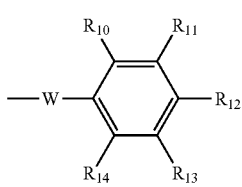

in which W is $(CH_2)_n$ (n=0 to 3); $SO_2$ or CO;
Y is selected from O or NH;

R1, R2, R3, R4, R5, R6, R7, R8 and R9 are the same or different, and are selected from: H; F; Br; Cl; $CF_3$; CN; $NO_2$; $CH_3$; OH; $OCH_3$; $OCF_3$; $NH_2$; $N(CH_3)_2$; $COOCH_3$ and COOH;

R10, R11, R12, R13 and R14 are the same or different, and are selected from H; F; Br; Cl; $CF_3$; CN; $NO_2$; $CH_3$;OH; $OCH_3$; $OCF_3$; $NH_2$; $N(CH_3)_2$; $COOCH_3$; COOH; $(CH_2)_m CON(CH_3)_2$ (m=0 to 6) and $(CH_2)_m CON(CH_2 CH_3)_2$ (m=0 to 6).

In another preferred embodiment, the invention provides for exploiting the antiandrogenic properties of compounds according to above-mentioned formulae (A-1), (A-2), (A-3) and (A-4), such as using a compound according to formula (A-1), (A-2), (A-3) or (A-4) to, e.g., treat an androgen receptor-related disease; treat primary prostate cancer; treat advanced prostate cancer; etc. The invention in a preferred embodiment provides a method of treating a disease (such as, e.g., an androgen receptor-related disease, primary prostate cancer, advanced prostate cancer, etc.), the method comprising administration to a patient of a therapeutically effective amount of a compound according to formula (A-1), (A-2), (A-3) or (A-4):

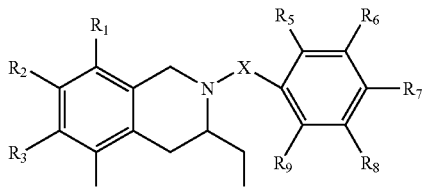

(A-1)

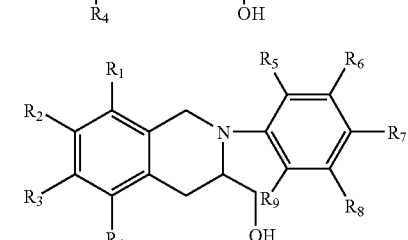

(A-2)

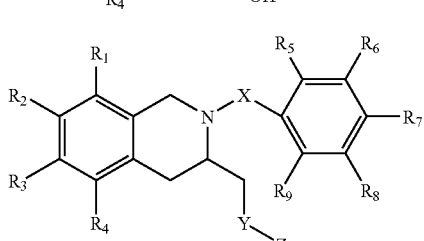

(A-3)

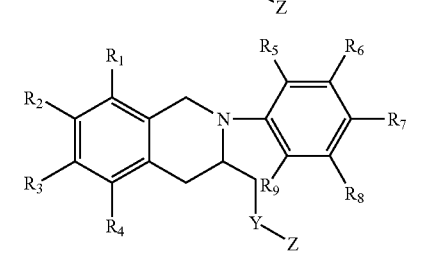

(A-4)

said formulae (A-1), (A-2), (A-3), (A-4) having definitions as above-mentioned.

In another preferred embodiment, the invention provides a method of treating an androgen receptor-related disease, comprising administration of a therapeutically effective amount of a compound selected from the group consisting of compound (A-1); compound (A-2); compound (A-3); compound(A-4); compound (A-5); compound (A-6); compound (A-7); compound (A-8); compound (A-9); compound (A-10); the compound of FIG. 8; compound 1b (FIGS. 8, 8A) and compound 1h (FIGS. 8, 8A) to a patient suffering from an androgen receptor-related disease.

In a further preferred embodiment, the invention provides a method of treating prostate cancer, comprising administration of a therapeutically effective amount of a compound selected from the group consisting of compound (A-1); compound (A-2); compound (A-3); compound (A-4); compound (A-5); compound (A-6); compound (A-7); compound (A-8); compound (A-9); compound (A-10); the compound of FIG. 8; compound 1b (FIGS. 8, 8A) and compound 1h (FIGS. 8, 8A) to a patient suffering from prostate cancer.

Figure 1:
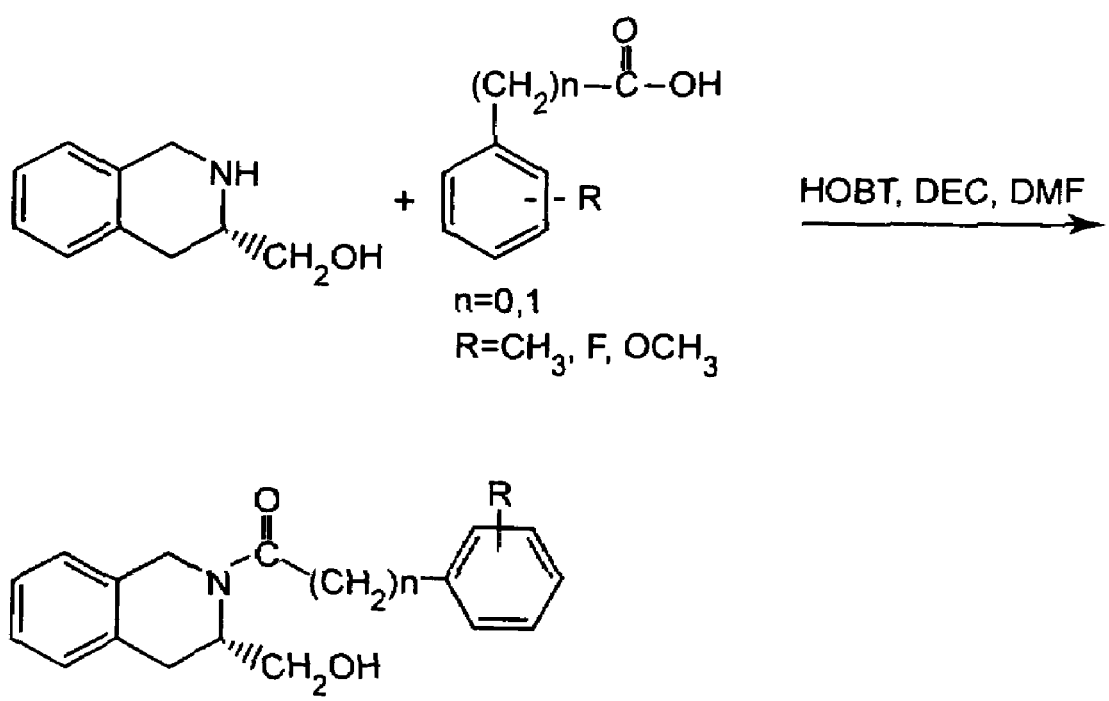
FIG. 1. Schematic synthesis scheme.
Figure 2:
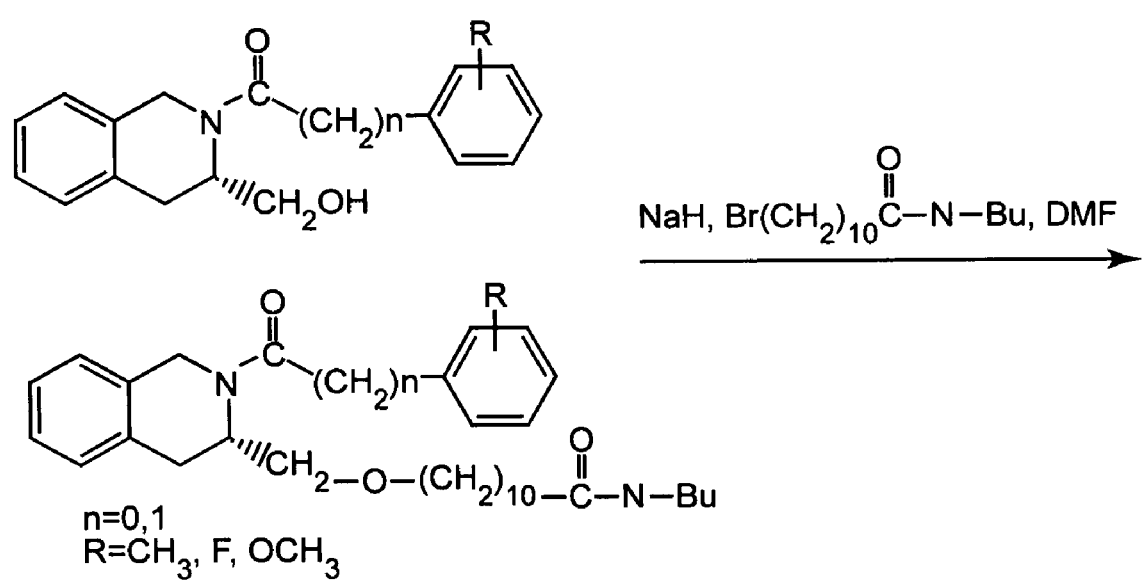
FIG. 2. Schematic synthesis scheme.
Figure 3:
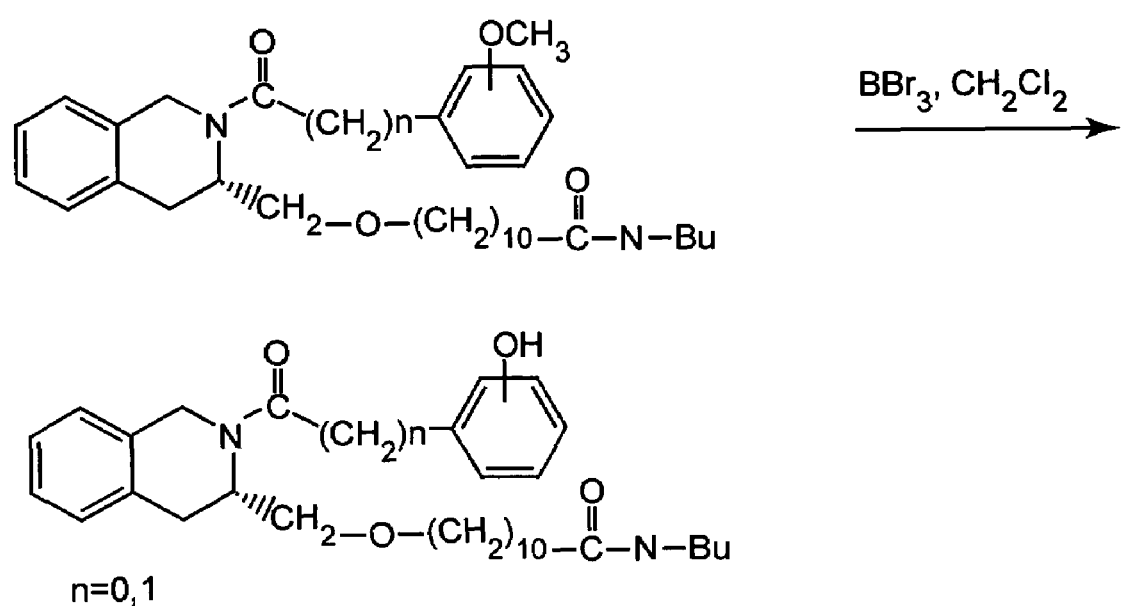
FIG. 3. Schematic synthesis scheme.

The relative luciferase activity was quantified as RLA of 10 μM tested compound/RLA of 10 μM CDCA. The RLA was average of at least three determinations.

DETAILED DESCRIPTION OF THE PREFERRED EMBODIMENTS OF THE INVENTION

A series of compounds possessing antiestrogenic and tissue-selective estrogenic properties have been discovered. The compounds are tetrahydroquinoline phenylamide derivatives and may be used in the treatment of estrogen receptor related diseases, including breast and prostate cancer. In particular, the compounds will be of use in the treatment of advanced breast cancer, especially when tamoxifen (or other treatments modalities) have ceased to be effective. Currently, tamoxifen can be used to treat breast cancer for only about five years due to the development of tamoxifen resistance by the tumor cells. Unfortunately, it has been discovered that the related compound raloxifene may be cross-resistant to tamoxifen-resistant breast tumors, eliminating it as a potential alternative treatment. The compounds of the present invention, which are not cross-resistant to tamoxifen-resistant breast tumors, thus provide another much needed avenue of alternative treatment.

Further, apart from their usefulness as a cancer treatment, the compounds of the present invention will be also useful in the treatment of osteoporosis in a manner similar to tamoxifen.

The compounds of the present invention offer the advantage that they are easy to prepare compared to commercial products based on naturally occurring molecules (e.g. tamoxifen).

The compounds are based on the generic structure depicted in Formula 1:

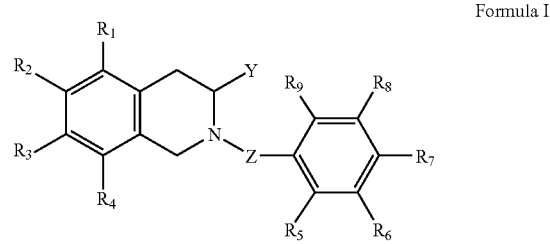

Formula I in which

Z is selected from CO, $CH_2$, and $(COCH_2)n$, where n=1 or 2;

R1, R2, R3, R4, R5, R6, R7, R8 and R9 are the same or different, and are selected from H, OH, halogens, R and OR, where R is a substituted or unsubstituted alkyl group having 1-4 carbons;

Y is selected from —$CH_2$—O—R10 and —$CH_2$—NH—R10;

R10 is selected from:

1) —$(CH_2)$n-C(=O)—N—R11, R12, where n=1-10 and R11 and R12 are the same or different, and are selected from: substituted and unsubstituted $C_1$-$C_9$ alkyl, substituted and unsubstituted cycloalkyl, and substituted and unsubstituted aryl;

2) —$(CH_2)$n-S(=O)—N—R11, R12, where n=1-10 and R11 and R12 are the same or different, and are selected from: substituted and unsubstituted $C_1$-$C_9$ alkyl, substituted and unsubstituted cycloalkyl, and substituted and unsubstituted aryl;

3) —$(CH_2)$n-$SO_2$—N—R11, R12, where n=1-10 and R11 and R12 are the same or different, and are selected from:

substituted and unsubstituted $C_1$-$C_9$ alkyl, substituted and unsubstituted cycloalkyl, and substituted and unsubstituted aryl;
4) —($CH_2$)n-S(=O)—R11, where n=1-10 and R11 s selected from: substituted and unsubstituted $C_1$-$C_9$ alkyl, substituted and unsubstituted cycloalkyl, and substituted and unsubstituted aryl;
5) —($CH_2$)n-$SO_2$—R11, where n=1-10 and R11 is selected from: substituted and unsubstituted $C_1$-$C_9$ alkyl, substituted and unsubstituted cycloalkyl, and substituted and unsubstituted aryl.

In a preferred embodiment of the invention, the substituted $C_1$-$C_9$ alkyl is —$CH_2CH_2CH_2CF_2CF_3$,
In other preferred embodiments, R1, R2, R3, R4, R5, R6, R7, R8 and R9 are selected from F, $OCH_3$, OOH, $CH_3$ and Cl.

The following compounds illustrate preferred embodiments of the invention:

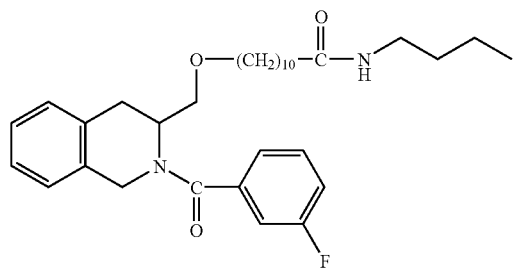

Formula 2. 11-[2-(3-Fluoro-benzoyl)-1,2,3,4-tetrahydro-isoquinolin-3-ylmethoxyl-undecanoic acid butylamide.

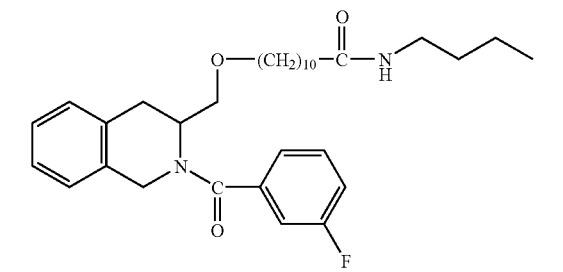

Formula 3. 11-[2-(3-Fluoro-benzoyl)-6-hydroxy-1,2,3,4-tetrahydro-isoquinolin-3-ylmethoxyl-undecanoic acid butylamide.

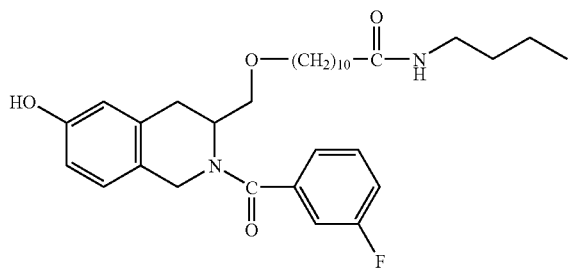

Formula 4. 11-[2-(3-Fluoro-benzoyl)-7-hydroxy-1,2,3,4-tetrahydro-isoquinolin-3-ylmethoxyl-undecanoic acid butylamide.

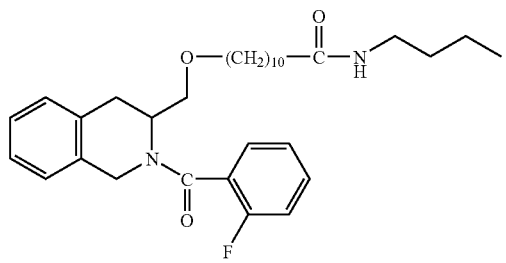

Formula 5. 11-[2-(2-Fluoro-benzoyl)-1,2,3,4-tetrahydro-isoquinolin-3-ylmethoxyl-undecanoic acid butylamide.

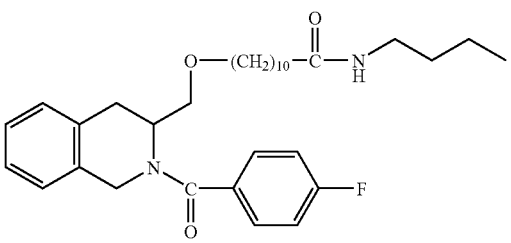

Formula 6. 11-[2-(4-Fluoro-benzoyl)-1,2,3,4-tetrahydro-isoquinolin-3-ytmethoxyl-undecanoic acid butylamide.

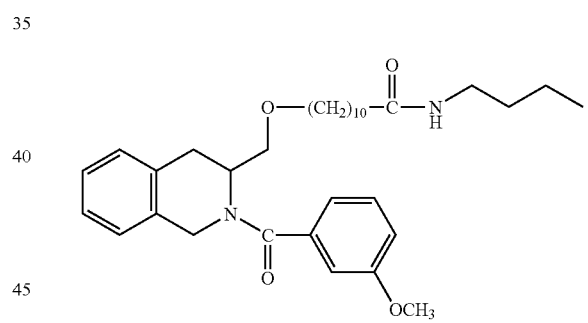

Formula 7. 11-[2-(3-Methoxy-benzoyl)-1,2,3,4-tetrahydro-isoquinolin-3-ylmethoxyl-undecanoic acid butylamide.

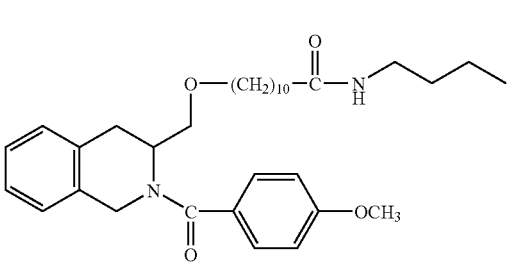

Formula 8. 11-[2-(4-Methoxy-benzoyl)-1,2,3,4-tetrahydro-isoquinolin-3-ylmethoxyl-undecanoic acid butylamide.

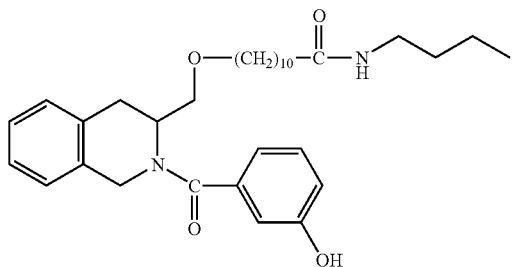

Formula 9. 11-[2-(3-Hydroxy-benzoyl)-1,2,3,4-tetrahydro-isoquinolin-3-ylmethoxyl-undecanoic acid butylamide.

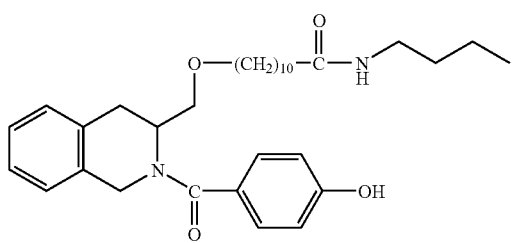

Formula 10. 11-[2-(4-Hydroxy-benzoyl)-1,2,3,4-tetrahydro-isoquinolin-3-ylmethoxyl-undecanoic acid butylamide.

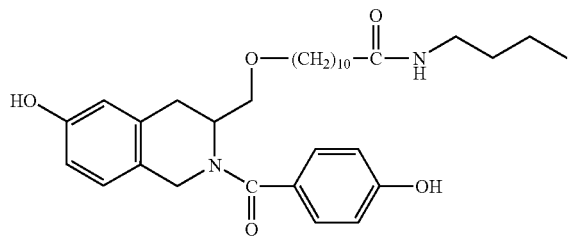

Formula 11. 11-[6-Hydroxy-2-(4hydroxy-benzoyl)-1,2,3,4-tetrahydro-isoquinolin-3-ylmethoxyl-undecanoic acid butylamide.

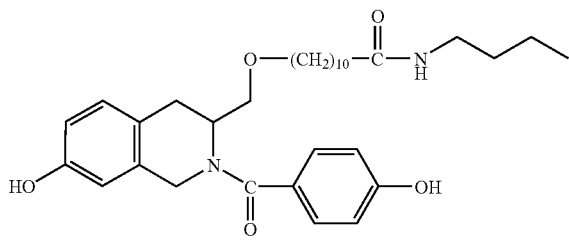

Formula 12. 11-[7-Hydroxy-2-(4-hydroxy-benzoyl)-1,2,3,4-tetrahydro-isoquinolin-3-ylmethoxyl-undecanoic acid butylamide.

Formula 13. 9-[6-Hydroxy-2-(4-hydroxy-benzoyl)-1,2,3,4-tetrahydro-isoquinolin-3-ylmethoxyl-nonanoic acid butylamide.

Formula 14. 9-[7-Hydroxy-2-(4-hydroxy-benzoyl)-1,2,3,4-tetrahydro-isoquinolin-3-ylmethoxyl-nonanoic acid butylamide.

Formula 15. {6-Hydroxy-3-[8-(4,4,5,5,5-pentafluoro-pentane-1-sulfinyl)-octyloxymethyl]-3,4-dihydro-1H-isoquinolin-2-yl}-(4-hydroxy-phenyl)-methanone.

Formula 16. {7-Hydroxy-3-[8-(4,4,5,5,5-pentafluoro-pentane-1-sulfinyl)-octyloxymethyl]-3,4-dihydro-1H-isoquinolin-2-yl}-(4-hydroxy-phenyl)-methanone.

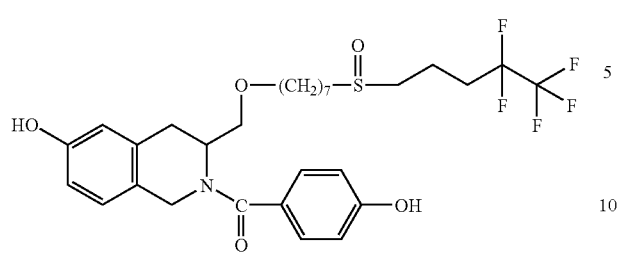

Formula 17. {6-Hydroxy-3-[7-(4,4,5,5,5-pentafluoro-pentane-1-sulfinyl)-heptyloxymethyl]-3,4-dihydro-1H-isoquinolin-2-yl}-(4-hydroxy-phenyl)-methanone.

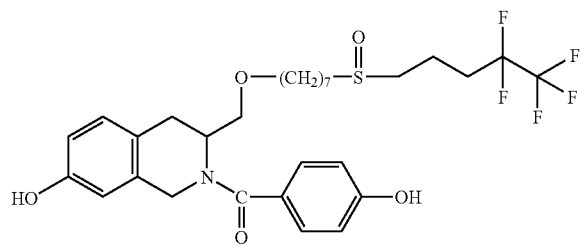

Formula 18. {-Hydroxy-3-[7-(4,4,5,5,5-pentafluoro-pentane-1-sulfinyl)-heptyloxymethyl]-3,4-dihydro-1H-isoquinolin-2-yl}-(4-hydroxy-phenyl)-methanone.

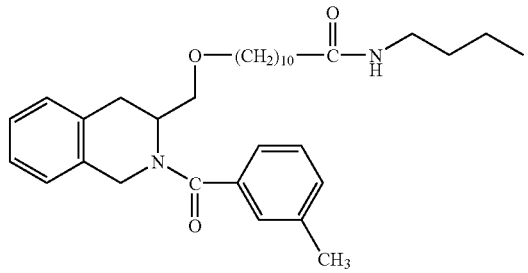

Formula 19. 11-[2-(3-Methyl-benzoyl)-1,2,3,4tetrahydro-isoquinolin-3-ylmethoxy]-undecanoic acid butylanide

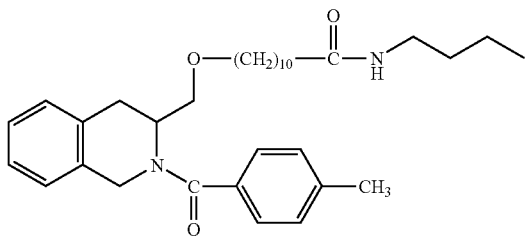

Formula 20. 11-[2-(4-Methyl-benzoyl)-1,2,3,4-tetrahydro-isoquinolin-3-ylmethoxy]-undecanoic acid butylamide

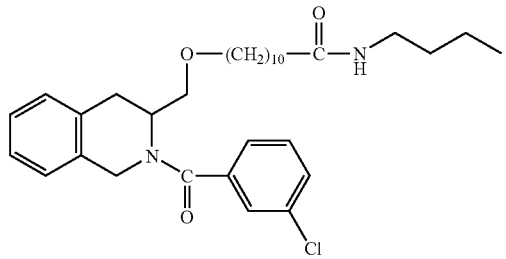

Formula 21. 11-[2-(3-Chloro-benzoyl)-1,2,3,4tetrahydro-isoquinolin-3-ylmethoxy]-undecanoic acid butylamide

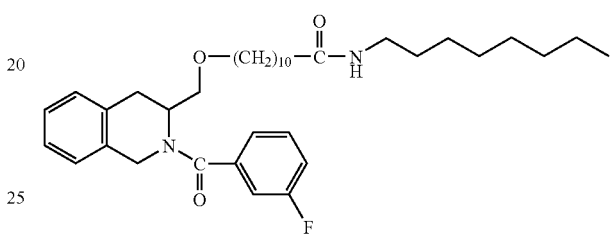

Formula 22. 11-[2-(3-Fluoro-benzoyl)-1,2,3,4-tetrahydro-isoquinolin-3-ylmethoxy]-undecanoic acid butylamide

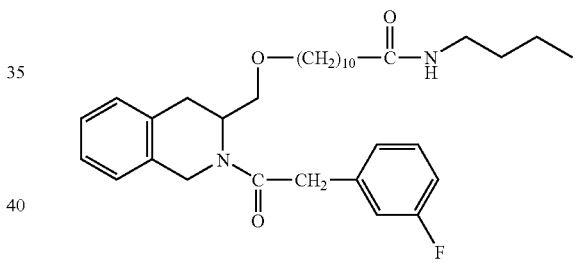

Formula 23. 11-{2-[2-(3-Fluoro-phenyl)-acetyl]-1,2,3,4-tetrahydro-isoquinolin-3-ylmethoxy]-undecanoic acid butylamide The present invention provides methods for the treatment of diseases involving estrogen receptors. In a preferred embodiment of the invention, the disease is breast cancer. In another embodiment of the invention, the disease is prostate cancer. By "breast cancer" and "prostate cancer" we mean both tumors that develop in the breast/prostate, and metastatic tumors that originated in breast/prostate tissue. By "treating" cancer we mean that a compound is administered in order to alleviate symptoms of the disease (e.g. to slow or stop growth of a tumor or to decrease tumor size, halt metastasis, etc.). Those of skill in the art will recognize that, in the treatment of cancer, administration of the compounds of the present invention may completely eradicate symptoms of the disease, or, alternatively, may attenuate or slow the progression of disease, which is also beneficial to the patient.

In particular, the compounds of the present invention may be useful for the treatment of breast cancer tumors that are resistant to tamoxifen.

In yet another embodiment of the invention, the disease that is treated is osteoporosis. By "treating" osteoporosis we mean that a compound is administered in order to alleviate symptoms of the disease (e.g. to increase bone density, or at least to prevent, stop or slow the loss of bone density). Those of skill in the art will recognize that, in the treatment of osteoporosis, administration of the compounds of the present invention may completely eradicate symptoms of the disease, or, alternatively, may attenuate or slow the progression of disease, which is also beneficial to the patient.

Use of the compounds will generally involve identifying patients suffering from estrogen-receptor related tumors (e.g. breast or prostate tumors), or alternatively, from osteoporosis, and administering the compounds in an acceptable form by an appropriate route. Administration may be oral or parenteral, including intravenously, intramuscularly, subcutaneously, etc., or by other routes (e.g. transdermal, sublingual, aerosol, suppository, etc.).

The compounds can be administered in the pure form or in a pharmaceutically acceptable formulation including suitable elixirs, binders, and the like or as pharmaceutically acceptable salts or other derivatives. It should be understood that the pharmaceutically acceptable formulations and salts include liquid and solid materials conventionally utilized to prepare injectable dosage forms and solid dosage forms such as tablets and capsules. Water may be used for the preparation of injectable compositions which may also include conventional buffers and agents to render the injectable composition isotonic. Other potential additives include: colorants; surfactants (TWEEN, oleic acid, etc.); and binders or encapsulants (lactose, liposomes, etc). Solid diluents and excipients include lactose, starch, conventional disintergrating agents, coatings and the like. Preservatives such as methyl paraben or benzalkium chloride may also be used. Depending on the formulation, it is expected that the active composition will consist of 1-99% of the composition and the vehicular "carrier" will constitute 1-99% of the composition. The pharmaceutical compositions of the present invention may include any suitable pharmaceutically acceptable additives or adjuncts to the extent that they do not hinder or interfere with the therapeutic effect desired of the Pt complex.

The administration of pharmaceutical compositions of the present invention can be intermittent, or at a gradual or continuous, constant or controlled rate to a patient. In addition, the time of day and the number of times per day that the pharmaceutical formulation is administered can vary. Further, the preferred dosing schedule can vary depending upon factors such as the mode of delivery, gender, age, and other conditions of the patient, as well as tumor type, stage, grade and location.

The dosage to be administered may vary depending on the age, gender, weight and overall health status of the individual patient, as well as the nature of the cancer itself. The level of efficacy and optimal amount of dosage may vary somewhat from compound to compound.

EXAMPLES

Experimental Methods and Materials

A. Synthesis of N-Butyl-11-bromoundecanamide

11-Bromoundecanoic acid (45 mmol) was dissolved in dry $CH_2Cl_2$ (200 ml) and tributylamine (54 mmol). After the mixture had cooled at $-10°$ C., isobutylchlorofomate (60 mmol) was added and allowed to react for 2 hrs. At this moment, excess N-butylamine (225 mmol) was added and later the cooling bath was removed. After 3 hrs, $CH_2Cl_2$ was added and the organic phase was washed with 1 N HCl, saturated $NaHCO_3$, and water. After drying by $MgSO_4$, the solvent was removed and the crude product was purified by column chromatography. The pure amide product was eluted with solvent, hexane (80)—EtOAc (20).

The purified amide was further crystallized with hexane.

General Procedures for the Synthesis of Compounds of the Invention, Designated Compounds 1-13

Relative benzoic acid (phenyl acetic acid) and (s)(−)-1,2,3,4-tetrahydro-3-isoquinoline methanol were dissolved in DMF under nitrogen gas. The 1-hydroxybenzotriazole hydrate (HOBT) and 1-(3-(Dimethylamino) propyl)-3-ethylcarbodiimide) hydrochloride (DEC) were added into the solution and the reaction were stirred further. After 16 hrs, EtOAc was added into reaction solution and the solution was washed with 10% $KHSO_4$, saturated $NaHCO_3$, and brine. The resulted organic phase was dried by $MgSO_4$. The crude product was purified by column chromatography. The purified compound was dissolved in DMF, NaH and N-butyl-11-bromoundecanamide was added into solution. The reaction solution was refluxed under nitrogen gas further. After 16 hrs, EtOAc was added into reaction solution and the solution was washed with $H_2O$ and brine. The resulted organic phase was dried by $MgSO_4$. The crude product was further purified by column chromatograph to generate final pure product.

11-[2-(2-Fluoro-benzoyl1) 1,2,3,4-tetrahydro-isoquinolin-3-ylmethoxy]-undecanoic acid butylamide (compound 11): Yield: 71%; $^1$H NMR(CDCl$_3$, 300 MHz): δ0.95 (t, 3H, CH$_3$), 1.1-1.3 (m, 14H, CH$_2$), 1.35-1.48 (m, 2H, CH$_2$), 1.35-1.48 (m, 4H, CH$_2$), 2.16-2.18(m, 2H, C(O)CH$_2$), 2.75 (m, 2H, CH$_2$), 3.1-3.26 (m, 4H, OCH$_2$ and NCH$_2$), 3.41-3.52 (m, 2H, OCH$_2$), 4.19 (s, broad, 1H, CH), 4.42 (s, 2H, NCH$_2$), 6.92 (dd, 1H, ArH), 7.05-7.15 (m, 3H, ArH), 7.28-7.31 (m, 2H, ArH), 7.32-7.43 (m, 2H, ArH); Anal. Calcd. for $C_{32}H_{45}FN_2O_3$: C, 73.25; H, 8.64; N, 5.34. Found: C, 73.05; H, 8.41; N, 5.14.

11-[2-(3-Fluoro-benzoyl)-1,2,3,4-tetrahydro-isoquinolin-3-ylmethoxy]-undecanoic acid butylamide (compound 12): Yield: 68%; $^1$H NMR(CDCl$_3$, 300 MHz): δ0.93 (t, 3H, CH$_3$), 1.2-1.3 (m, 14H, CH$_2$), 1.36-1.51 (m, 2H, CH$_2$), 1.58-1.61 (m, 4H, CH$_2$), 2.14 (t, 2H, C(O)CH$_2$), 2.6 (m, 2H, CH$_2$,), 3.13-3.20 (m, 2H, NCH$_2$), 3.24 (t, 2H, OCH$_2$), 3.70-3.75 (m, 2H, OCH$_2$), 3.95-4.1 (m, 3H, CH and NCH$_2$), 6.78 (m, 1H, ArH), 7.15 (m, 3H, ArH), 7.28 (m, 3H, ArH), 7.47 (s, 1H, ArH); Anal. Calcd. for $C_{32}H_{45}FN_2O_3$: C, 73.25; H, 8.64; N, 5.34. Found: C, 73.13; H, 8.38; N, 5.21.

11-[2-(4-Fluoro-benzoyl)-1,2,3,4-tetrahydro-isoquinolin-3-ylmethoxy]-undecanoic acid butylamide (compound 13): Yield: 70%; $^1$H NMR(CDCl$_3$, 300 MHz): δ0.88 (t, 3H, CH$_3$), 1.2-1.28 (m, 14H, CH$_2$), 1.43-1.49 (m, 2H, CH$_2$), 1.59-1.62 (m, 4H, CH$_2$), 2.14 (m, 2H, C(O)CH$_2$), 2.69 (m, 2H, CH$_2$), 3.11-3.16 (m, 2H, NCH$_2$), 3.23 (t, 2H, OCH$_2$), 3.42 (m, 2H, OCH$_2$), 4.36 (m, 3H, CH and NCH$_2$), 7.06 (m, 1H, ArH), 7.10-7.14 (m, 3H, ArH), 7.19 (m, 2H, ArH), 7.45-7.49 (m, 2H, ArH); Anal. Calcd. for $C_{32}H_{45}FN_2O_3$: C, 73.25; H, 8.64; N, 5.34. Found: C, 73.08; H, 8.33; N, 5.18.

11-[2-(3-Methoxy-benzoyl)-1,2,3,4-tetrahydro-isoquinolin-3-ylmethoxy]-undecanoic acid butylamide (compound 14): Yield: 71%; $^1$H NMR(CDCl$_3$, 300 MHz): δ0.91 (t, 3H, CH$_3$), 1.27-1.47 (m, 16H, CH$_2$), 1.53-1.58 (m, 4H, CH$_2$), 2.12 (t, 2H, C(O)CH$_2$), 2.65 (m, 2H, CH$_2$), 3.2-3.3 (m, 4H, OCH$_2$ and NCH$_2$), 3.61 (d, 2H, OCH$_2$. J=6Hz), 3.82, (s, 3H, OCH$_3$), 4.27-4.37 (m, 2H, CH and NCH$_2$), 6.95-7.01 (m, 4H, ArH), 7.12-7.19 (m, 2H, ArH), 7.28-7.32 (m, 2H, ArH); Anal. Calcd. for $C_{33}H_4N_2O_4$: C, 73.84; H, 9.01; N, 5.22. Found: C, 73.58; H, 8.77; N, 5.03.

11-[2-(4-Methoxy-benzoyl)-1,2,3,4-tetrahydro-isoquinolin-3-ylmethoxy]-undecanoic acid butylamide (compound 15): Yield: 73%; $^1$H NMR(CDCl$_3$, 300 MHz): δ0.95 (t, 3H, CH$_3$), 1.30 (m, 14H, CH$_2$), 1.51 (m, 2H, CH$_2$), 1.65 (m, 4H, CH$_2$), 2.17 (t, 2H, C(O)CH$_2$), 2.74 (m, 2H, CH$_2$), 3.26 (m, 4H, OCH$_2$ and NCH$_2$), 3.45-3.47 (m, 2H, OCH$_2$), 3.89 (s, 3H, OCH$_3$), 4.35-4.50 (m, 2H, CH and NCH$_2$), 6.95-6.98 (m, 4H, ArH), 7.26-7.30 (m, 2H, ArH), 7.46 (m, 2H, ArH); Anal. Calcd. for C$_{33}$H$_{48}$N$_2$O$_4$: C, 73.84; H, 9.01; N, 5.22. Found: C, 73.64; H, 8.89; N, 5.08.

11-[2-(3-Hydroxy-benzoyl)-1,2,3,4-tetrahydro-isoquinolin-3-ylmethoxy]-undecanoic acid butylamide (compound 16): Yield: 58%; $^1$H NMR(CDCl$_3$, 300 MHz): δ0.91 (t, 3H, CH$_3$), 1.33-1.66 (m, 20H, CH$_2$), 2.18(t, 2H, C(O)CH$_2$), 2.74 (m, 2H, CH$_2$), 3.11 (m, 2H, NCH$_2$), 3.4 (m, 2H, OCH$_2$), 3.75 (m, 2H, OCH$_2$), 4.36 (m, 3H, CH and NCH$_2$), 6.85 (m, 1H, ArH), 6.88 (m, 1H, ArH), 7.08-7.19 (m, 5H, ArH), 7.4 (s, 1H, ArH); Anal. Calcd. for C$_{32}$H$_{46}$N$_2$O$_4$: C, 73.53; H, 8.87; N, 5.36. Found: C, 73.21; H, 8.72; N, 5.51.

11-[2-(4-Hydroxy-benzoyl)-1,2,3,4-tetrahydro-isoquinolin-3-ylmethoxy]-undecanoic acid butylamide (compound 17): Yield: 55%; $^1$H NMR(CDCl$_3$, 300 MHz): δ0.92 (t, 3H, CH$_3$), 1.27 (m, 14H, CH$_2$), 1.29-1.59 (m, 6H, CH$_2$), 2.19 (t, 2H, C(O)CH$_2$), 2.74 (m, 2H, CH$_2$), 3.34-3.41 (m, 4H, OCH$_2$ and NCH$_2$), 3.65 (m, 2H, OCH$_2$), 4.4 (m, 3H, CH and NCH$_2$), 6.84 (m, 2H, ArH), 7.18 (m, 3H, ArH), 7.32 (m, 3H, ArH); Anal. Calcd. for C$_{32}$H$_{46}$N$_2$O$_4$: C, 73.53; H, 8.87; N, 5.36. Found: C, 73.58; H, 8.63; N, 5.41.

11-[2-(3-Methyl-benzoyl)-1,2,3,4-tetrahydro-isoquinolin-3-ylmethoxy]-undecanoic acid butylamide (compound 18): Yield: 75%; $^1$H NMR(CDCl$_3$, 300 MHz): δ0.91 (t, 3H, CH$_3$), 1.26 (m, 14H, CH$_2$), 1.43-1.45 (m, 2H, CH$_2$), 1.58 (m, 4H, CH$_2$), 2.12 (t, 2H, C(O)CH$_2$), 2.38 (s, 2H, CH$_3$), 2.68 (m, 2H, CH$_2$), 3.18-3.29 (m, 4H, OCH$_2$ and NCH$_2$), 3.41-3.44 (m, 2H, OCH$_2$), 4.2 (m, 3H, CH and NCH$_2$), 6.88 (s, broad, 11H, ArH), 7.05-7.27 (m, 7H, ArH); Anal. Calcd. for C$_{33}$H$_{48}$N$_2$O$_3$: C, 76.11; H, 9.29; N, 5.38. Found: C, 75.98; H, 9.37; N, 5.57.

11-[2-(4-Methyl-benzoyl)-1,2,3,4-tetrahydro-isoquinolin-3-ylmethoxy]-undecanoic acid butylamide (compound 19): Yield: 71%; $^1$H NMR(CDCl$_3$, 300 MHz): δ0.91 (t, 3H, CH$_3$), 1.26 (m, 14H, CH$_2$), 1.40-1.45 (m, 2H, CH$_2$), 1.59 (m, 4H, CH$_2$), 2.11 (t, 2H, (O)CH$_2$), 2.67 (m, 2H, CH$_2$), 3.10-3.23 (m, 4H, OCH$_2$ and NCH$_2$), 3.40-3.44 (m, 2H, OCH$_2$), 4.28-4.48 (m, 3H, CH and NCH$_2$), 6.89 (s, broad, 1H, ArH), 7.10-7.21 (m, 5H, ArH), 7.34 (m, 2H, ArH); Anal. Calcd. for C$_{33}$H$_{48}$N$_2$O$_3$: C, 76.11; H, 9.29; N, 5.38. Found: C, 75.87; H, 9.58; N, 5.43.

11-[2-(3-Chloro-benzoyl)-1,2,3,4-tetrahydro-isoquinolin-3-ylmethoxy]-undecanoic acid butylamide (compound 20): Yield: 77%; $^1$H NMR(CDCl$_3$, 300 MHz): δ0.92 (t, 3H, CH$_3$), 1.27-1.35 (m, 14H, CH$_2$), 1.43-1.49 (m, 2H, CH$_2$), 1.62 (m, 4H, CH$_2$), 2.15 (t, 2H, C(O)CH$_2$), 2.65 (m, 2H, CH$_2$), 3.13-3.16 (m, 2H, NCH$_2$), 3.25 (t, 2H, OCH$_2$), 3.40 (d, 2H, OCH$_2$,J=8.4Hz), 4.28-4.34 (m, 1H, CH), 4.45 (s, 2H, NCH$_2$), 6.92 (m, 1H, ArH), 7.12-7.20 (m, 3H, ArH), 7.35-7.41 (m, 3H, ArH), 7.49 (s, 1H, ArH); Anal. Calcd. for C$_{32}$H$_{45}$ClN$_2$O$_3$: C, 71.02; H, 8.38; N, 5.18. Found: C, 71.28; H8.53; N, 5.01.

11-[2-(3-Fluoro-benzoyl)-1,2,3,4-tetrahydro-isoquinolin-3-ylmethoxy]-undecanoic acid octylamide (compound 21): Yield: 69%; $^1$H NMR(CDCl$_3$, 300 MHz): δ0.88 (t, 3H, CH$_3$), 1.26 (m, 22H, CH$_2$), 1.48 (m, 2H, CH$_2$), 1.61 (m, 4H, CH$_2$), 2.14 (t, 2H, C(O)CH$_2$), 2.64 (m, 2H, CH$_2$), 3.21-3.25 (m, 4H, OCH$_2$ and NCH$_2$), 3.41 (m, 2H, OCH$_2$), 4.29 (m, 1H, CH), 4.34 (s, 2H, NCH$_2$), 6.90 (m, 11H, ArH), 7.12-7.2 (m, 6H, ArH), 7.38 (s, 11H, ArH); Anal. Calcd. for C$_{36}$H$_{53}$FN$_2$O$_3$: C, 74.44; H, 9.20; N, 4.82. Found: C, 74.28; H, 9.36; N, 4.91.

11-{2-[2-(3-Fluoro-phenyl)-acetyl]-1,2,3,4-tetrahydroisoquinolin-3-ylmethoxy}-undecanoic acid butylamide (compound 22): Yield: 53%; $^1$H NMR(CDCl$_3$, 300 MHz): δ0.92 (t, 3H, CH$_3$), 1.25 (m, 14H, CH$_2$), 1.45-1.47 (m, 2H, CH$_2$), 1.61-1.66 (m, 4H, CH$_2$), 2.13 (t, 2H, C(O)CH$_2$), 2.85 (m, 2H, CH$_2$), 3.02 (s, 2H, C(O)CH$_2$), 3.23 (m, 4H, OCH$_2$ and NCH$_2$), 3.33 (m, 2H, OCH$_2$), 4.31 (s, broad, 1H, CH), 4.46 (s, 2H, NCH ), 6.89-6.99 (m, 4H, ArH), 7.05-7.15 (m, 4H, ArH); Anal. Calcd. for C$_{33}$H$_{47}$FN$_2$O$_3$: C, 73.57; H, 8.79; N, 5.20. Found: C, 73.67; H, 8.50; N, 4.91.

B. Biological Assays

Plasmid Preparation

The plasmids employed were the mammalian expression plasmid containing full length human ER cDNA, pCMV-hER, ER cDNA, pcDNA3.1-hER, human AIB1 cDNA, pcDNA3.1-AIB1 and the reporter gene expression plasmid containing three repeated estrogen receptor response elements, pGL-TATA-Luc. These four plasmids were used in the transient transfection reporter assays for estrogen receptor in human breast cancer cells. The yeast expression plasmid pCu424CUP1 and reporter gene plasmid pLG 178 for yeast-based human estrogen receptor reporter assays were purchased from ATCC (American Type Culture Collection Manassas, Va.). The yeast expression plasmids, pGADT7 and pGBTT7, for yeast two-hybrid assay were purchased from Clontech (Palo Alto, Calif.). The vector pCu424CUP1 is constructed to express human estrogen receptor. pCUP-hER contains full length hER cDNA and can express hER in yeasts BJ3505. The expression of hER is regulated by CUP1 promoter. For the construction of pCUP-hER, the hER cDNA was generated by PCR and the primers, 5'-GGATCCATGACCATGACCCTCCACACC-3' (SEQ ID NO. 1) and 5'-GTCGACTCAGACTGTGGCAGGAAACCC-3' (SEQ ID NO. 2) were designed by inserting a BamHI site in front of the hER start codon and a SalI site after the hER stop codon. The pCMV-hER was used as the template of the PCR reaction. The resulting PCR product was further cloned into pCu424CUP1 between BamHI site and SalI site to generate pCUP-hER. pCUP-hER contains long form full length hER cDNA and can express hER in yeasts BJ3505. The expression of hER is also regulated by CUP1 promoter.

For the construction of pCUP-hER, the hER cDNA was generated by PCR and the primers, 5'-GGATCCATG-GATATAAAAAACTCACCATC-3' (SEQ ID NO. 3) and 5'-GTCGACTCACTGAGACTGTGGGTTCTGG-3' (SEQ ID NO. 4) were designed by inserting a BamHI site in front of the hER start codon and a SalI site after the hER stop codon. The pcDNA3.1-hER was used as the template of the PCR reaction. The PCR product was subsequently cloned into pCu424CUP1 between BamHI site and SalI site to generate pCUP-hER. The vectors, pGBKT7 and pGADT7 were used to perform yeast two-hybrid assays for hER. pGBKT7 contains the Gal-4 DNA binding domain which was fused with the bait protein. pGADT7 containing the Gal-4 activation domain which was fused further with the target protein. pGBT-hER contains full length hER cDNA and can express Gal4 DNA binding/hER in yeasts Y190. For the construction of pGBT-hER, the hER cDNA was generated by PCR and the primers, 5'-CATATGACCATGACCCTCCACACC-3' (SEQ ID NO. 5) and 5'-GGATCCTCAGACTGTGGCAGGAAACCC-3' (SEQ ID NO. 6) were designed by inserting an NdeI site in front of the hER start codon and a BamHI site after the hER stop codon. The PCR product was cloned into pGBKT7 between NdeI and BamHI site. pGAD-hER contains full length hER cDNA and can express hER conjugated with Gal4 activation domain in yeasts Y190. For the construction of pGAD-hER, the hER was generated by PCR which used the same primers mentioned in the construction of pGBT-hER. The PCR product was cloned into pGADT7 between NdeI and BamHI site.

The vector, pLG 178 was used to construct reporter gene in yeast based estrogen receptor reporter transactivation assays. There are three repeated estrogen receptor response element GGTCACGCTGACC cloned in front of lacZ, reporter gene. The cDNA of three repeated ERE was generated by PCR in which the plasmid pERE3-TATA-CAT was used as the template. The primers, 5'-CTCGAGTGGTTTTTGAC-CCCGAACG-3' (SEQ ID NO. 7) and 5'-CTCGAGC-CCGGGGTCTAGAAGATCC-3'(SEQ ID NO. 8), used in generating PCR product were designed by inserting XhoI site at 5' and 3' terminus. The PCR product was cloned into pLG 178 within XhoI sites to generate pLG 178ERE3. The sequence of all plasmids was confirmed by DNA sequence reactions performed by Iowa State University DNA sequencing facility (Ames, Iowa).

Yeast Strains

The *S. cerevisiae* strain BJ3505 (MAT pep4: His3 prb1-1.6R his3-200 lys2-801 ura3-52 gal2 can1) obtained from ATCC was used in the estrogen receptor reporter transactivation assays. The yeast strain Y190 (MATa leu2-3 leu2-112 ura3-52 trp1-901 his3-200 ade2-101 gal4 gal80 ura3 Gal-lacZ lys gal-his3 cyhR) obtained from ATCC was used in the yeast two-hybrid assays. All yeast transformation was carried out following the lithium acetate transformation protocol.

Site-directed Mutagenesis

The tyrosine mutation (pCMV-D351Y) at amino acid 351 was introduced by using the Quick Change Site-Directed Mutagenesis Kit (Stratagene, La Jolla, Calif.) and pCMV-ER was used as the template. The primers constructed were as follows: 5' primer (5'-GGCTTACTGACCAACCTGGCATA-CAGGGAGCTGGTTCAC-3') (SEQ ID NO. 9), the underlined nucleotide was changed to make the D351Y mutation) and a 3' primer (5'-GTGAACCAGCTCCCTGTATGCCAG-GTTGGTCAGTAAGCC-3') (SEQ ID NO. 10).

Reporter Gene Transactivation and β-galactosidase Assays for Human Estrogen Receptor in Yeast The transformed yeasts from early-mid-log phase growth (OD600 nm approximately 1.0) were diluted to an OD600 nm of 0.03 in selective medium plus 50 M $CuSO_4$ to induce estrogen receptor production. The diluted yeasts were aliquoted into 15-ml cap tubes containing culture medium 5 ml per tube and doses of either estradiol or test molecules, or both in methanol or DMSO were added. A solvent (methanol or DMSO) control was included in each experiment. The cultures were incubated overnight at 30 C with vigorous orbital shaking (300 rpm). After incubation, the yeast samples were diluted in appropriate selective medium to OD600 of 0.3-0.4 and 100 μl was added to each well of a 96-well microtiter plate. Each sample was assayed in triplicate. To each well, 100 μl of assay buffer (60 mM $Na_2HPO_4$, 40 mM $NaH_2PO_4$, 10 mM KCl, 1 mM $MgSO_4$, 2mg/ml 2-nitrophenyl-beta-D-galactosidase (ONPG), 0.1% SDS, 50 mM -mercaptoethanol, and 200U/1 oxalyticase (Enzogenetics, Corvallis, Oreg.) was added. The change of ortho nitrophenol, the yellow product that resulted from β-galactosidase cleavage of ONPG, was measured by using a kinetic microtiter plate reader (Molecular Device, Sunnyvale, Calif.). -galactosidase activity is expressed as Vmax (mOD420/min) divided by cell density (OD590). The relative activity for test samples is the β-galactosidase activity of test sample over that of estradiol whose activity is 1.

Yeast Two-hybrid and Filter Lift Assays

The transformed yeasts with yeast two-hybrid vectors were cultured in synthetic medium lacking trytophan, and leucine. The estradiol or/and test molecule was added to the cultured medium after the transformed yeast cells were plated on nitrocellulose membrane. After stimulation with estradiol or test molecules for overnight, the nitrocellulose membranes plated with yeast cells were transferred to a new filter and the yeast cells were permeablized by three heat-freeze cycles. After that, the membranes were soaked in 0.4 ml Z-buffer/Xgal (60 mM $Na_2HPO_4$, 40 mM $NaH_2PO_4$ 10 mM KCl, 1 mM $MgSO_4$, 0.1% SDS, 50 mM -mercaptoethanol, 20 mM Xgal). The pictures of the results were taken within 2 and 3 hours after the -galactosidase assay was processed.

Chemiluminescence-based Competitive Binding Assay

The HitHunter™ EFC estrogen receptor chemilinescence assay kit (Discoverx, Fremont, Calif.) was used to determine the ability of test molecules to displace ED-estrogen conjugate from hERα-ED-estrogen conjugate complex. The recombinant hER or hER (5 nM) was preincubated with ED-estrogen conjugate in screening buffer. After the preincubation, the test molecules and hER-ED-estrogen conjugate complex solution were added into the 96-well microplate to produce a final volume of 50 μl per well. After the reaction was incubated at room temperature for 1.5 hrs, the EA solution and chemiluminescence substrate buffer were added into each well for 1 hr incubation, and the luminescence values were measured by using luminescence microplate reader, LumiCount (Packard, Boston, Mass.). The $IC_{50}$ value of tested compounds was generated by graphfit software. The $IC_{50}$ value was further converted to relative binding affinity (RBA) by using raloxifene's $IC_{50}$ as the standard that was set to 1. The RBA value of each test molecule was calculated by using the equation; RBA equals ($IC_{50}$ of raloxifene/$IC_{50}$ of test molecule).

Fluorescence-based Competitive Binding Assays

The estrogen receptor competitor assay kits (Panvera, Madison, Wis.) were used to determine the ability of test molecules to displace the fluormone, ES2, from hER -ES2 or hER -ES2 complex. Serial dilutions of each test molecule were prepared in methanol or DMSO. The recombinant hER or hER (7 nM) was preincubated with ES2 (1 nM) in screening buffer. After the preincubation, the test molecules and ER-ES2 complex solution were added into the 96-well microplate to produce a final volume of 100 μl per well. The reaction was incubated at room temperature for 1 hr and the polarization values were measured by using fluorescence microplate reader, Polarion (Tecan, Research Triangle Park, N.C.) with excitation wavelength 495 nm and emission wavelength 535 nm. The polarization value versus test molecule concentration curves was analyzed by graphfit software to generate $IC_{50}$ values. The $IC_{50}$ value was further converted to relative binding affinity (RBA) by using tamoxifen's $IC_{50}$ as the standard that was set to 1. The RBA value of each test molecule was calculated by using the equation; RBA equals ($IC_{50}$ of tamoxifen/$IC_{50}$ of test molecule).

Cell Culture, Transfection, Luciferase Assay and β-galactosidase Assay

Human breast cancer cells, MCF-7 (ER positive) and MDA-MB-231(ER negative), were purchased from ATCC. The cells routinely were cultured as monolayer in Dulbecco's modified minimal essential medium (GIBCO/BRL, Grand Island, N.Y.) supplemented with 10% fetal bovine serum (Hyclone, Logan, Utah), Penicillin (100 unit/ml)/Streptomycin (100 g/ml) and bovine insulin (0.005 mg/ml) (GIBCO/

BRL, Grand Island, N.Y.), and incubated at 37° C. in a humidified atmosphere of 5% $CO_2$/air.

For the transient transfection reporter assays, the cells were plated in triplicate in 12-well plates at a density of 300000 cells/well in the phenol red-free DMEM (GIBCO/BRL, Grand Island, N.Y.) supplemented with 10% charcoal-stripped fetal bovine serum (Hyclone, Logan, Utah), Penicillin (100 unit/ml)/Streptomycin (100 g/ml), 2 mML-glutamine and 1 mM sodium Pyruvate. 24 hrs later, the cells were transfected with three plasmids by using Superfect transfection kit (Qiagen, Valencia, Calif.). For the detection of hER activity, cells were transfected with 2 g hER expression plasmid (pCMV-ER ), 6 g luciferase reporter plasmid containing estrogen receptor response element (PGL-TATA-Luc), and 600 ng normalization control, β-galactosidase reporter plasmid (pCMV ). For the detection of hER activity, cells were transfected with 3 ug hER expression plasmid (pcDNA3.1-hER), 6 g luciferase reporter plasmid containing estrogen receptor response element (PGL-TATA-Luc), and 600 ng pCMV. For determining the influence of ER's major coactivator in breast, AIB 1, 2 g pcDNA3.1-AIB1 was added into the transfection plasmid solution mentioned previously.

The transfected cells were rinsed with PBS and treated with various concentrations of test molecules and one positive control (vehicle, DMSO or methanol) in phenol red-free culture medium. After incubation for further 24 hrs, the cells were washed with PBS and lysed with lysis buffer (Pierce, Rockford, Ill.). The lysate was used to determine the luciferase activity for ER's activity and the β-galactosidase activity for the normalization of transfection efficiency.

For the luciferase activity assay, 20 μl of lysate and 100 μl luciferase assay buffer (Promega, Madison, Wis.) were added into a well of 96-well plate. The luminescence was detected by using luminescence microplate reader, LumiCount (Packard, Boston, Mass.). For the β-galactosidase activity assay, 20 ml of lysate and 185 ml β-galactosidase assay buffer (Clontech, Palo Alto, Calif.) were added into a well of 96-well plate. The β-galactosidase activity was measured as luminescence strength by using luminescence microplate reader, LumiCount (Packard, Boston, Mass.). The normalized reporter activity was calculated by the luciferase activity divided by that of β-galactosidase. For the estrogenic or antiestrogenic effects of test molecules, the normalized reporter activity value was further converted to relative normalized reporter activity by using the value of estradiol or DMSO as a standard that was set to 1.

Cell Proliferation Assay

MCF-7 or MDA-MB-231 cells were inoculated into 12-well culture plates at 10000 cells in 2 ml maintained medium per well. Cells were allowed to attach to the bottom for 24 hrs incubation, then the seeding medium was removed and replaced by the experimental medium (phenol red-free DMEM supplemented with 5% charcoal-stripped fetal bovine serum and Penicillin (100 unit/ml)/Streptomycin (100 g/ml)). After 24 hr incubation, the test molecules dissolved in DMSO were added in the wells. The final concentration of DMSO in the culture medium did not exceed 0.1%. The culture was continued for 3 days and the medium and tested compounds were replaced every two days. The final cell numbers were estimated with CellTiter proliferation assay kit (Promega, Madison, Wis.) by measuring the absorbance at 570 nm, which is directly proportional to the number of living cells in the culture. Experiments were at least duplicated for each compound and the results are shown as average value of at least three individual testing with less than 15% error.

Results and Discussion

Fluorescence-based Binding Affinity Testing for Compounds of the Invention

In this assay, recombinant hER and the commercial synthetic estrogen, ES2 containing fluorescence polarization property, are used. This assay is a homogenous assay. When the assay solution only contains ES2, the solution exerts weak fluorescence polarization property due to the quick rotation of free ES2 molecule. On the contrary, when ES2 is mixed with hER, the rotation of ES2 is largely decreased due to its tight interaction with hER and the solution exerts strong fluorescence polarization property. Addition of the antiestrogen to the ES2/hER displaces ES2 from hER and results in the whole solution exerting less fluorescence polarization property than the solution without antiestrogen. Based on this principle, the higher the binding affinity of the tested compound, the lower fluorescence polarization value the tested solution would exert.

Table 1 shows the relative binding affinity of certain compounds of the present invention, designated compounds 1 to 12, where generic Tamoxifen was tested as reference and its binding affinity was set at 1. The result showed that among these compounds, compounds 6 and 7 have highest binding affinity and higher than tamoxifen. The preferable physical property of the substituted group on the second aromatic ring is hydrogen bond donor and hydrogen bond acceptor, and the favorable tendency of substituent's physical property for binding affinity is $OH > F > OCH_3 > CH_3, Cl$. For the substituted position on the second aromatic ring, substituents at 3'-position are slightly better than 4'-position and 2'-position is the least preferred for binding. Essentially, when the binding affinity of compounds 2, 11 and 12 are compared, it reveals that the length of the bridge and side chain seem not to influence the compound's binding affinity.

TABLE 1

Relative binding affinity of compound 1 to compound 12 for hER in fluorescence-based binding assay

| Compound | n | $R_1$ | $R_2$ | Relative Binding Affinity |
|---|---|---|---|---|
| 1 (Formula 5) | 0 | 2'-F | butyl | 0.225 |
| 2 (Formula 2) | 0 | 3'-F | butyl | 0.287 |
| 3 (Formula 6) | 0 | 4'-F | butyl | 0.264 |
| 4 (Formula 7) | 0 | 3'-$OCH_3$ | butyl | 0.192 |
| 5 (Formula 8) | 0 | 4'-$OCH_3$ | butyl | 0.14 |
| 6 (Formula 9) | 0 | 3'-OH | butyl | 5.0 |
| 7 (Formula 10) | 0 | 4'-OH | butyl | 1.79 |
| 8 (Formula 19) | 0 | 3'-$CH_3$ | butyl | 0.156 |
| 9 (Formula 20) | 0 | 4'-$CH_3$ | butyl | 0.132 |
| 10 (Formula 21) | 0 | 3'-Cl | butyl | 0.156 |
| 11 (Formula 22) | 0 | 3'-F | octyl | 0.177 |
| 12 (Formula 23) | 1 | 3'-F | butyl | 0.267 |
| Tamoxifen | | | | 1 |

Transient Transfection Reporter Testing

Figure 4:
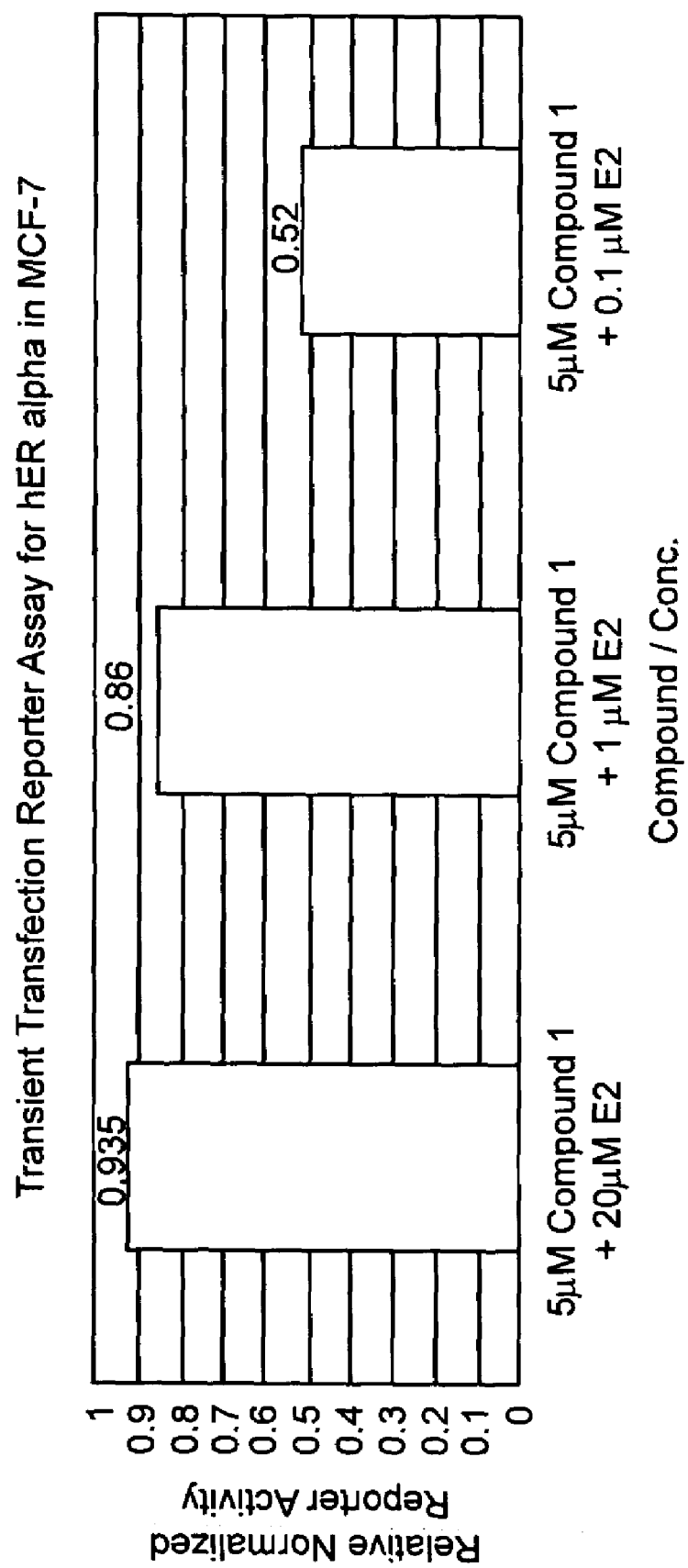
FIG. 4. Antiestrogenic activity of compound 1 against various concentrations of estrogen in transient transfection reporter assay for hERα in MCF-7 cells.

The transient transfection reporter assay was used to determine the estrogenic or antiestrogenic activity of tested compounds in employed human breast cancer cells, MCF-7 cells that are cotransfected with hERα expression and reporter plasmids. For estrogenic activity, 5 μM tested compound was added to transfected MCF-7 cells. For antiestrogenic activity, 5 µM tested compound and 1 nM estradiol are added to transfected MCF-7 cells. The estrogenic (antiestrogenic) activity was determined by dividing the luciferase activity by the β-galactosidase activity. To determine the influence of estrogen receptor's major coactivator in breast cancer, AIB1, for the compounds' estrogenic activity, the expression vector of AIB1 was additionally cotransfected with the plasmids mentioned above. The results are shown in FIG. 4. As can be seen, compound 1 can antagonize estrogen's action in a dose dependent manner.

Table 2 shows the estrogenic effects of compounds 1 to 12. In the same assay, DMSO was tested as reference and its estrogenic effect was set as 1. Tamoxifen and estrogen were also tested for comparison. Shown in the Table 2, tamoxifen's relative estrogenic effect is 1.385. Among the compounds 1 to 12, compound 7 exerts the highest estrogenic effect. Apart from compound 7, compounds 8, 9 and 12 have similar or higher estrogeic effects than tamoxifen. The other compounds 1, 2, 3, 4, 5, 6, 10 and 11 do not exert any estrogenic effects. Essentially, those compounds containing substituent on the 3' position of the second aromatic ring don't possess estrogenic effects, except compound 8 containing methyl group on the 3 position and compound 12 with longer bridge length. For compound containing hydroxyl group and compound 9 containing methyl group on the 4' position of the second aromatic ring, both exert significant estrogenic effects.

TABLE 2

Relative estrogenic activity of compound 1 to 12 in transient transfection reporter assay for hERα in MCF-7 cells

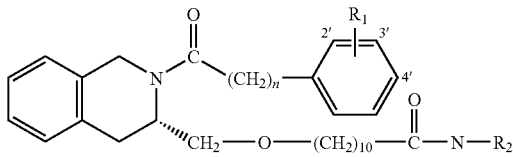

| Compound | n | $R_1$ | $R_2$ | Relative Estrogenic Activity at 2.5 mM |
|---|---|---|---|---|
| 1 (Formula 5) | 0 | 2'-F | butyl | 1.02 |
| 2 (Formula 2) | 0 | 3'-F | butyl | 0.9 |
| 3 (Formula 6) | 0 | 4'-F | butyl | 1.09 |
| 4 (Formula 7) | 0 | 3'-OCH$_3$ | butyl | 0.78 |
| 5 (Formula 8) | 0 | 4'-OCH$_3$ | butyl | 1.06 |
| 6 (Formula 9) | 0 | 3'-OH | butyl | 1.03 |
| 7 (Formula 10) | 0 | 4'-OH | butyl | 2.05 |
| 8 (Formula 19) | 0 | 3'-CH$_3$ | butyl | 1.32 |
| 9 (Formula 20) | 0 | 4'-CH$_3$ | butyl | 1.72 |
| 10 (Formula 21) | 0 | 3'-Cl | butyl | 0.68 |
| 11 (Formula 22) | 0 | 3'-F | octyl | 0.83 |
| 12 (Formula 23) | 1 | 3'-F | butyl | 1.68 |
| DMSO | | | | 1 |
| Tamoxifen | | | | 1.385 |
| 1 nM E2 | | | | 5.92 |

Table 3 shows the antiestrogenic effects of several compounds of the present invention. In this assay, 1 nM estrogen was used as reference and tamoxifen was tested for comparison. The compounds 2, 4, 6, 7, 8 and 10 showed 25% to 56% inhibition against estrogen, and tamoxifen showed 72% inhibition activity. Compound 6 containing hydroxyl moiety on the 3' position of the second aromatic ring, had the strongest inhibition activity among the compounds and the rest of the compounds with the substituent on the 3' position of the second aromatic ring showed moderate inhibition activity, except compound 12. Compound 7 with hydroxyl group on the 4' position also exhibited moderate antiestrogenic activity. Based on the physical property of the substituents, hydrogen bond donor group, like hydroxyl, was optimal, and hydrogen bond acceptor group, like fluoro and methoxy, was secondly optimal. Unexpectedly, compound 8 with methyl group substituent on the 3 position exerts moderate antiestrogenic effect and it also possesses a moderate estrogenic effect.

TABLE 3

Relative antiestrogenic of compound 1 to 12 in transient transfection reporter assay for hERα in MCF-7 cells

| Compound | n | $R_1$ | $R_2$ | Relative Antiestrogenic Activity at 2.5 µM |
|---|---|---|---|---|
| 1 (Formula 5) | 0 | 2'-F | butyl | 1.17 |
| 2 (Formula 2) | 0 | 3'-F | butyl | 0.75 |
| 3 (Formula 6) | 0 | 4'-F | butyl | 0.93 |
| 4 (Formula 7) | 0 | 3'-OCH$_3$ | butyl | 0.79 |
| 5 (Formula 8) | 0 | 4'-OCH$_3$ | butyl | 1.64 |
| 6 (Formula 9) | 0 | 3'-OH | butyl | 0.44 |
| 7 (Formula 10) | 0 | 4'-OH | butyl | 0.76 |
| 8 (Formula 19) | 0 | 3'-CH$_3$ | butyl | 0.75 |
| 9 (Formula 20) | 0 | 4'-CH$_3$ | butyl | 1.34 |
| 10 (Formula 21) | 0 | 3'-Cl | butyl | 0.83 |
| 11 (Formula 22) | 0 | 3'-F | octyl | 1.11 |
| 12 (Formula 23) | 1 | 3'-F | butyl | 1.01 |
| Tamoxifen | | | | 0.28 |
| 1 nM E2 | | | | 1 |

Amino acid 351 (D351) of hERα plays an essential role in regulating estrogenic or antiestrogenic compound's binding to hERα and the recruitment of corepressors. Importantly, the point mutation of D351 to tyrosine (Y) was found to occur in tamoxifen treated breast tumors. The mutated D351Y can largely enhance 4-hydroxytamoxifen's estrogenic activity so the D351Y hERα mutant is implied to serve a key function for the formation of tamoxifen resistant breast tumors. Based on this observation the hERα D351Y mutant is generated by PCR-based site directed mutagenesis method for use in the transient transfection reporter assay. The main goal of this testing is to elucidate the existence of the pure antiestrogenic property of the compounds of the invention and to determine whether the compounds estrogenic activity will increase due to the presence of hERα D351Y or not.

Figure 5:
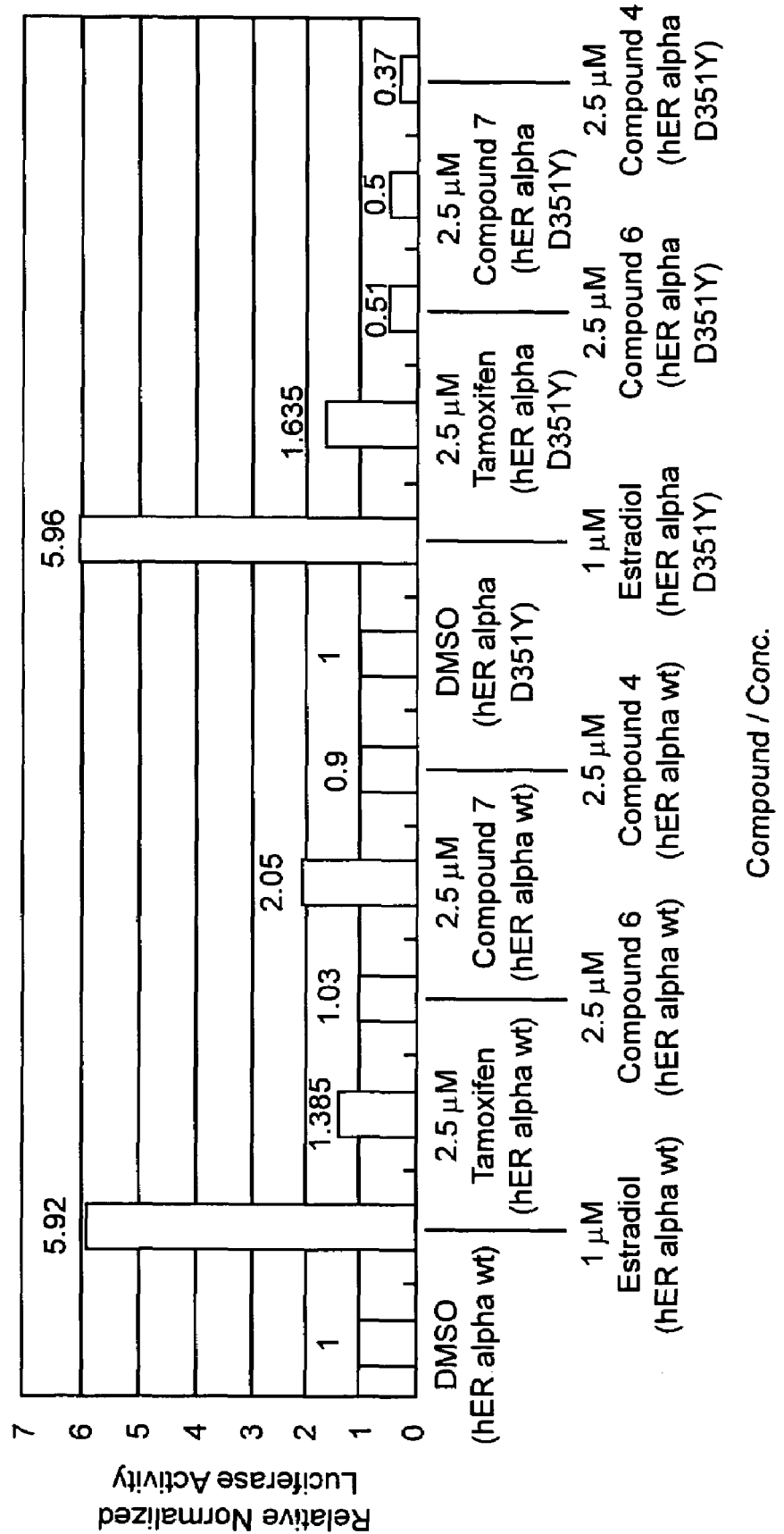
FIG. 5. Estrogenic activity comparison of compounds 4, 6 and 7 for wild type hERα and hERα D351Y in transient transfection receptor assay.

FIG. 5 shows the estrogenic activity of compounds 4, 6, and 7 against hERα D351Y. In this assay, DMSO was used as reference. Estrogen and tamoxifen were used as the comparison. The results shown in FIG. 5 indicate that the estrogenic activity of estrogen does not increase and that of tamoxifen only moderately increases. However, the estrogenic activitys of compounds 4, 6, and 7, do not increase when their estrogenic effects against hERα D351Y and hERα wild type are compared. Interestingly, the estrogenic effects of compounds 4, 6, and 7 against mutant hERα D351Y are even lower than that of DMSO.

This result demonstrates that these compounds can act as pure antiestrogens and they provide antiestrogenic effects against basal hERα effects.

hERα Positive Breast Cancer Cell Proliferation Testing for Compounds 1-13

MCF-7 cell line was used to perform this assay and the description of this assay as mentioned above. Table 4 shows the inhibition activity of compounds 1 to 13 against MCF-7 cell proliferation. DMSO was used as reference. Estrogen and tamoxifen are also tested for comparison.

2 nM estrogen stimulates the growth of DMSO-treated MCF-7 cells 150% compared to 58% by tamoxifen. For compounds 1 to 13, compounds 3, 8 and 10 only show slight inhibition effects. Compound 6 exerts the strongest inhibition effects with 38% inhibition. However, compounds 2 and 4 exert slightly lower inhibition effects than compound 6. The results show that the compounds with substituent on the 3' position of the second aromatic ring exert much better anti-proliferation activity against hERα dependent breast cancer cells than those with substituent on the 4' position. The relationship between physical property of substituent and anti-proliferation activity is that hydrogen bond donor>hydrogen bond acceptor>hydrophobic group. This trend correlates with the trend from transient transfection reporter assay's antiestrogenic testing. In fact, those compounds that show good antiestrogenic effects in transient transfection reporter assay also possess good anti-proliferation activity against MCF-7 cells.

These results confirm that compounds of the present invention exhibit inhibition ability against hERα.

TABLE 4

Proliferation effects of compound 1 to 13 against MCF-7 cells

| Compound | n | $R_1$ | $R_2$ | Relative Cancer Cell Proliferation Effects at 5 μM |
|---|---|---|---|---|
| 1 (Formula 5) | 0 | 2'-F | butyl | 1.06 |
| 2 (Formula 2) | 0 | 3'-F | butyl | 0.66 |
| 3 (Formula 6) | 0 | 4'-F | butyl | 0.91 |
| 4 (Formula 7) | 0 | 3'-OCH$_3$ | butyl | 0.7 |
| 5 (Formula 8) | 0 | 4'-OCH$_3$ | butyl | 0.98 |
| 6 (Formula 9) | 0 | 3'-OH | butyl | 0.62 |
| 7 (Formula 10) | 0 | 4'-OH | butyl | 0.95 |
| 8 (Formula 19) | 0 | 3'-CH$_3$ | butyl | 0.84 |
| 9 (Formula 20) | 0 | 4'-CH$_3$ | butyl | 1.01 |
| 10 (Formula 21) | 0 | 3'-Cl | butyl | 0.86 |
| 11 (Formula 22) | 0 | 3'-F | octyl | 1 |
| 12 (Formula 23) | 1 | 3'-F | butyl | 1.2 |
| 13 (not depicted) | 0 | 4'-CF$_3$ | butyl | 1.01 |
| DMSO | | | | 1 |
| Tamoxifen | | | | 0.42 |
| 2 nM E2 | | | | 1.52 | hER Negative Breast Cancer Cell Proliferation Testing for Compounds 2, 4 and 6

In this assay, MDA-MB-231 breast cancer cell line, a hER negative cell line, was used. DMSO was used as reference. Estrogen and tamoxifen were also tested for comparison.

Figure 6:
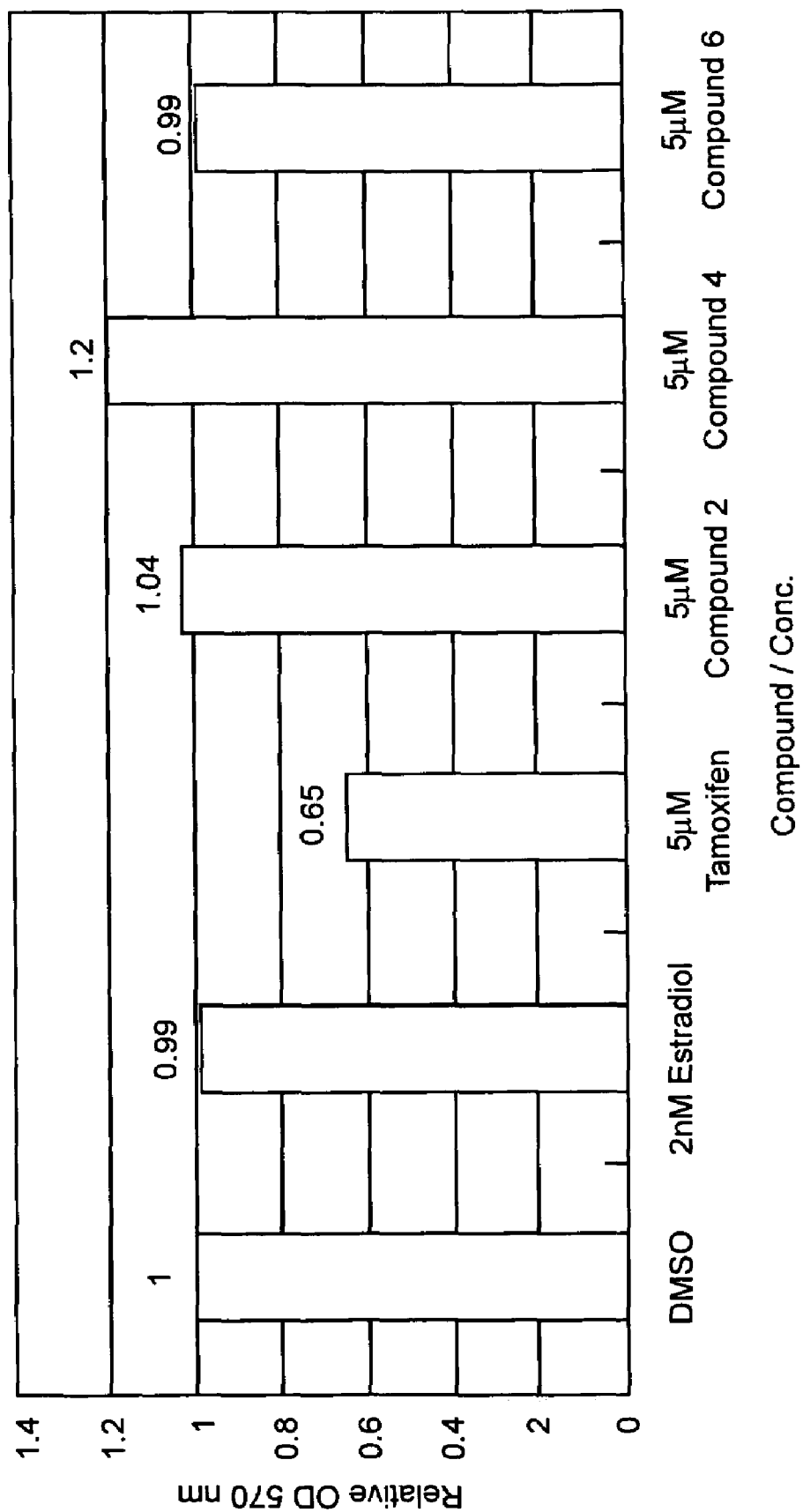
FIG. 6. Proliferation effects of compounds 2, 4 and 6 against MDA-MB-231 cells.

FIG. 6 shows the proliferation activities of compounds 2, 4 and 6. As expected, estrogen 10 does not promote the growth of MDA-MB-231 cells. Compounds 2, 4, and 6 also do not inhibit or stimulate the growth of MDA-MB-231 cells. However, tamoxifen still exerts moderate anti-proliferation effects against MDA-MB-231 cells. Tamoxifen's ER independent anti-proliferation activity has been proposed by several groups.

The results shown here further demonstrate that the inhibitory effects of compounds 2, 4, and 6 against hERα are specific.

Yeast Two-hybrid/Filter Lifting Testing for Compounds 2 and 6

Dimerization of estrogen receptor plays an essential role in regulating estrogen receptor's functions including DNA binding, transactivation, and coactivator recruitment. In this study, yeast two hybrid and filter lift assays were used to determine the ability of compounds 2 and 6 to interrupt the dimerization of hERα. For setting up yeast two hybrid assay, the full length hERα was inserted into pGAD-GAL4 and pGBD-GAL4 vectors. In pGBD-GAL4, hERα was fused to the GAL4 DNA binding domain through its N terminus. In pGAD-GA14, hERα was fused to the GAL4 activation domain through its N terminus. When the dimerization of hERα occurs mainly through its C terminus, the GAL4 DNA binding domain binds to the repeated GAL4 response element located in front of the β-gal reporter gene and the whole complex, GAL4-BD/hERα/hERα/GAL4-AD, turns on the synthesis of the product of β-gal reporter gene. The compound's inhibitory activity is inversely related to the activity of the reporter gene product, β-galactosidase. The higher the activity of β-galactosidase, the lower the compound's inhibitory activity against hERα dimerization. Filter lift assay in which X-gal was used, was employed to qualitatively determine the activity of β-galactosidase. Increase in blue color formed from the tested yeast colony indicates that the tested compound does not possess significant inhibition activity.

Compound 2 and tamoxifen were tested either alone or in combination with estrogen. The results indicated that compound 2 and tamoxifen alone did not induce the dimerization of hERα based on the fact that their relative tested yeast colony did not change color. When combined with estrogen, both compounds exert only a weak inhibitory activity. Compound 6 and tamoxifen were also tested. The results showed that compound 6 and tamoxifen did not induce hERα dimerization. When estrogen's colony was used as a reference colony, the colony tested with compound 6 in combination with estrogen shows slight blue color change. However, the colony tested with tamoxifen in combination with estrogen shows moderate blue color change. Results observed for this test after one additional hour of color development further confirmed the result.

This result demonstrates that compound 6 can exert inhibitory activity against estrogen for the dimerization of hERα and its inhibitory activity is higher than tamoxifen's.

Since compound 6 has a hydrophobic side chain similar to ICI type of compounds, ICI182,780 (FIG. 7B) was also tested in this assay for comparison. The results showed that Compound 6 and ICI182,780 alone do not promote the dimerization of hERα. However, when combined with estrogen, both compounds exert an obvious inhibitory activity against the dimerization of hERα. Unexpectedly, compound 6's inhibitory activity is similar to that of ICI182,780.

Taken together, these experimental results demonstrate that the compounds of the present invention function in vivo and in vitro as competitive inhibitors of estrogen binding to estrogen receptors.

Anti-Androgen Examples

Referring to above-mentioned general formulae (A-1), (A-2), (A-3) and (A-4), the following are examples of compounds with anti-androgenic properties.

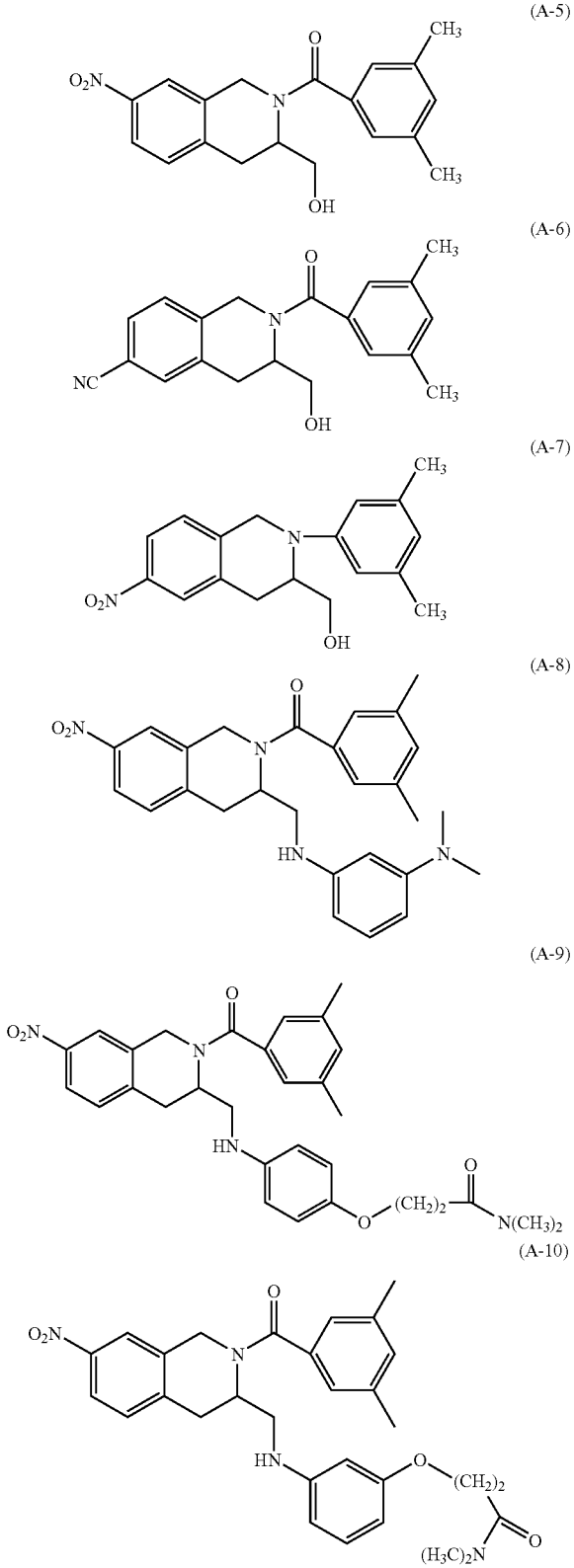

Further Background

Nuclear receptors act as transcription factors to modulate transcription actions of target genes involved in maintenance of cellular phenotypes, metabolism and cell proliferation, through homodimerizing or heterodimerizing with other nuclear receptors and until now, there are more than 30 members in the nuclear receptor superfamily. (Olefsky, J. M. Nuclear receptor minireview series. *J Biol. Chem.*, 276, 36863-36864,2001.) Most nuclear receptors exert their functions by ligand-activation and they usually contain four functional domains, from N-terminus to C-terminus, first transcription activation domain (AF-1), DNA binding domain, hinge domain and second transcription activation domain (AF-2) that is also the ligand binding domain. Because of their importance in these novel diseases, they are viewed as potential targets for the development of specific treatments against these diseases.

Prostate cancer is the most common type of non-skin cancer and the second leading cause of cancer death in American men. Androgens are steroid hormones that are responsible for the cellular proliferation and differentiation of male sexual organs and secondary sexual characteristics and their action is mainly exerted through a specific nuclear receptor androgen receptor (AR). (Culig, Z., Klocker, H., Bartsch, G., Hobisch, A. Androgen receptors in prostate cancer. *Endocrine-Related Cancer,* 9: 155-170 (2002).) Androgen exerts its effects via a genomic mechanism in which androgen passively enters the target cells and binds to AR in the cytoplasm. (Gao W., Bohl C. E., Dalton J. T. Chemistry and structural biology of androgen receptor. *Chem. Rev.*, 105: 3352-3370, 2005.) The formed androgen/AR complex dissociates from heat shock protein and further translocates into nucleus. In the nucleus, the AR complex dimerizes and binds to the promoter region of the androgen-regulated gene to initiate the transcription action and enhance the production of androgenregulated proteins, like PSA, Bc1-2 and maspin. (Luke, M. C., Coffey, D. S., Human androgen receptor binding to the androgen response element of prostate specific antigen. J. Androl., 15: 41-51 (1994); Huang, H., Zegarra-Moro, O. L., Benson, D., Tindall, D. J. Androgens repress Bc1-2 expression via activation of retinoblastoma (RB) protein in prostate cancer cells. Oncogene, 23: 2161-2176(2004); Zhang, M., Magit, D., Sager, R., Expression of maspin in prostate cells is regulated by a positive Ets element and a negative hormonal responsive element site recognized by androgen receptor, *Proc Natl Acad Sci,* 94: 5673-5678 (1997).

In the early stage of prostate cancer, its growth highly relies on the androgen and the use of androgen deprivation therapy can strongly slow down the growth rate of prostate cancer. Numerous compounds that act as AR agonists like R1881, or antagonists like flutamide, nilutamide, cyperoterone acetate (CPA) and biclutamide have been developed. (Rayes, B. F., Hussain, M. H. Hormonal therapy for prostate cancer: Past, present and future. *Expert Rev Anticancer Ther.,* 2: 37-47 (2002)) Although Flutamide has been used as the first line adjuvant monotherapy against prostate cancer for more than two decades, the patients who took flutamide may eventually encounter resistant stage. Therefore an urgent need exists to develop new types of antiandrogens. (Iversen, P., Melezinek, I., Schmidt, A. Nonsteroidal antiandrogens: a therapeutic option for patients with advanced prostate cancer who wish to retain sexual interest and function. BJU Int, , 87: 47-56 (2001). )

Farnesoid x receptor (FXR) is also a member of nuclear receptor superfamily whose endogenous ligand has been identified as numerous bile acids, including chenodeoxycholic acid (CDCA), CA, and DCA. (Chiang J. Y. Regulation of bile acid synthesis: pathways, nuclear receptors, and mechanism. *J Hepatol.* 17: 386-349 (2004).) The action of FXR is through heterodimerizing with another novel nuclear receptor, retinoid x receptor (RXR) to regulate the transcription of numerous essential genes involved in bile acid metabolism including small heterodimer partner 1 (SHP), cholesterol 7α hydroxylase (CYP7A1) and bile salt export pump (BSEP). (Goodwin B., Jone S. A., Price P. R., Watson M. A., McKee D. D., et al. A regulatory cascade of the nuclear receptor FXR, SHP-1 and LRH-1 represses bile acid biosynthesis. *Mol. Cell.* 6: 517-526 (2000); Chen W., Owsley E., Yang Y., Stroup D., Chiang J. Y. Nuclear receptor-mediated repression of human cholesterol 7alpha-hydroxylase gene transcription by bile acids. *J. Lipid Res.,* 42: 1402-1412, 2001; Ananthanarayanan M., Balasubramanian N., Makishima M., Mangelsdorf D. J., Suchy F. J. Human bile salt export pump promoter is transactivated by the farnesoid x receptor/bile acid receptor. *J Biol. Chem.,* 276: 28857-28865, 2001.) Because these genes regulated by FXR are involved in bile acid related diseases, FXR modulators are viewed as potential treatments for bile acid and cholesterol homeostasis diseases including cardiovascular and lipid metabolism diseases.

Experimentation

A series of new core scaffold, 1, 2, 3, 4, tetrahydroisoquinoline-N-phenylamide derivatives, were designed and evaluated for their activities against AR and FXR. This new core scaffold has a 3-D structure that may superimpose with that of steroid, like estrogen, so it was chosen as the core chemical skeleton to develop nuclear receptor modulators. For AR, most nonsteroidal antiandrogens contain two structural moieties, a cyano (or a nitro) and trifluoromethyl groups at the phenyl ring (A ring) of the core scaffold that mimic the A ring of testosterone, as well as a hydrogen bond donor moiety, like hydroxyl group, connected with their core scaffolds. The tetrahydroisoquinoline-N-phenylamide in this Experimentation is able to superimpose with the steroidal core scaffold of testosterone. Essentially, once this core scaffold is substituted by hydroxylethyl group at 3 position, this new scaffold can mimic the important moieties of flutamide and contains an additional phenylamide group that might locate within helix 5 as well as 11 to contribute extra binding affinity. In this Experimentation, we generated compounds designed by employing this new core scaffold substituted various hydrophobic or hydrophilic substituents on the additional phenylamide group. Because the goal of this Experimentation was to quickly determine whether this new designed scaffold can be used for serving as the lead pharmacohpore, we did not insert the conserved hydrogen bond donor to A ring of the scaffold as tamoxifen for estrogen receptor.

Additionally, for FXR, its native ligands like CDCA have steroidal core scaffold and our new core scaffold should also be able to fit into FXR ligand binding pocket so we also tested these compounds for FXR.

Synthesis

Figure 7:
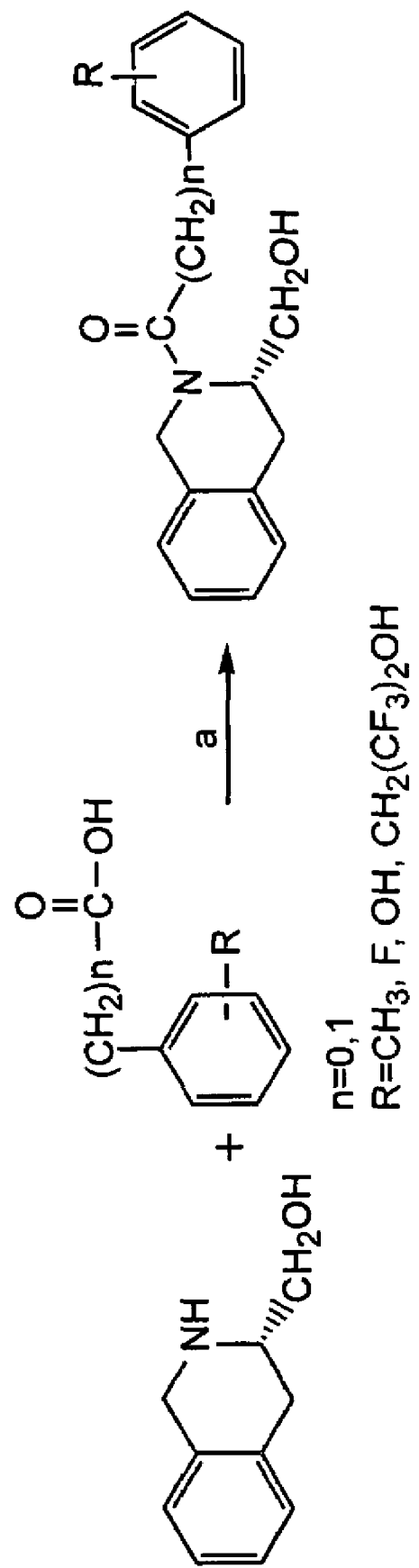
FIG. 7. Schematic synthesis scheme of compounds 1a-2b discussed herein, a: DEC, HOBT, DMF.
Figure 7A:
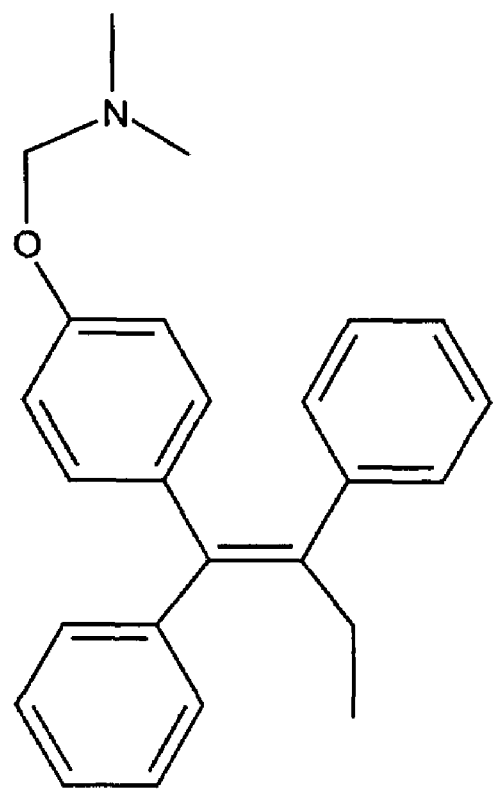
Figure 7B:
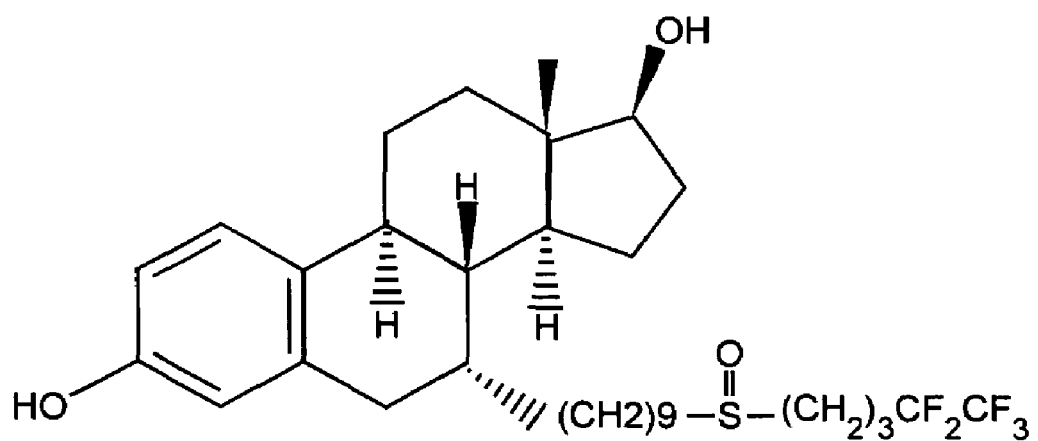

Compounds 1a to 2b were simply synthesized by mixing commercial benzoic acid or phenyl acetic acid derivatives, (s)-(−)-1, 2, 3, 4-tetrahydro-3-isoquinoline methanol, 1-hydroxybenzotriazole hydrate (HOBT) and 1-(3-(Dimethylamino) propyl)-3-ethyl-carbodiimide) hydrochloride (DEC) to react for overnight under nitrogen gas, as shown in the reaction scheme in FIG. 7.

For synthesis of compounds (A-5), (A-6), (A-7), (A-8), (A-9) and (A-10): for making a compound with the nitro group, $HNO_3/H_2SO_4$ is used. For the cyano group, the nitro group is formed, then $H_2/Pt$, $NaNO_2/HCl$, KCN is used.

Figures 8, 8A:
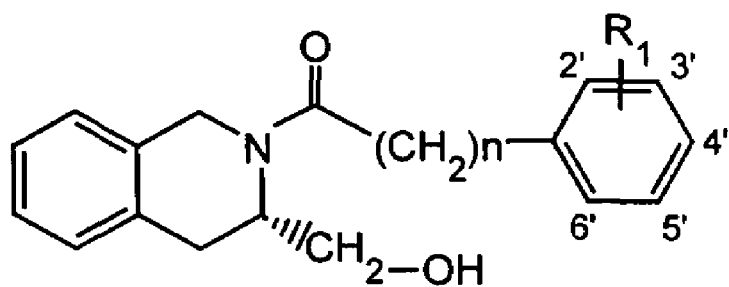
FIG. 8. A generic formula for chemical structures according to an embodiment of the invention, including compounds in the table in FIG. 8A.
FIG. 8A. Table showing results of a fluorescence polarization competitive binding assay with recombinant AR protein. AR binding: The polarization values verse test molecule concentration curves were analyzed by nonlinear least-squares curve fitting in the graphfit or prism software and generated IC50 value. The $IC_{50}$ value was further converted to relative binding affinity (RBA) by using flutamide's $IC_{50}$ as a standard. The RBA value of each test molecule was quantified as RBA=$IC_{50}$ of flutamide/ $IC_{50}$ of test molecule.

The table in FIG. 8A summarizes the relative binding affinity of compound 1a to 2b. The fluorescence-based competitive binding assay purchased from Panvera (Madison Wis.), uses a synthetic androgen with high fluorescence polarization property when it binds to AR and recombinant AR ligand binding domain fused with GST. After the individual binding affinity was determined, it was further calculated as relative binding affinity by employing flutamide as standard comparison. CPA was also tested as a reference. Thus, compounds 1a to 2b all showed higher binding affinity than flutamide but with less binding affinity than CPA. Among these compounds, 1h and 2b showed 12-fold higher binding affinity than flutamide. In the ligand binding pocket of AR, there are three essential hydrogen bond residues: (1) Arg 752 of helix 5 and Gln 711 of helix 3; (2) Asn 705 of helix 3; (3) Thr 877 of helix 11. (Matias P. M., Donner P., Coelho R., Egner U., Carrondo M. A. Structural evidence for ligand specificity in the ligand binding domain of the human androgen receptor. Implications for pathogenic gene mutations. *J Biol. Chem.,* 275: 26164-26171, 2000.) Apart from these residues, most residues lean toward binded ligand and are hydrophobic.

Most antiandrogens like flutamide and bicalutamide bind to AR-LBD mainly through their hydrogen bond acceptor like nitro or cyano group at the 4 position of their A ring to interact with Arg 752 and Gln 711 and a hydrogen bond donor hydroxyl group that is connected with their A ring, to form a second hydrogen bond interaction with Asn 705. Importantly, although the inventive compounds in FIG. 8A do not contain a hydrogen bond acceptor group on A ring, they still can bind to AR with moderate binding affinity. The key factor is believed to be the hydroxyl moiety of the hydroxymethyl group on the B ring of these compounds that might potentially engage in a hydrogen bond with the side-chain of residue Asn 705 or the amide backbone of Leu 704. This hydrogen bond interaction is similar to that shown in hydroxyflutamide's binding mode because this new core scaffold and hydroxyflutamide can superimpose well in the 3-hydroxymethyl-1, 2, 3, 4, tetrahydroisoquinoline structural portion. These compounds might adopt another orientation that the D ring of these compounds resides within the helix 3 and helix 5 and allow the substitution hydrophilic groups on D ring to interact with Arg 752 and Gln 711 as the A ring of flutamide. However, the structure-activity relationship of flutamide and bicalutamide derivatives demonstrated that the derivatives with cyano or nitro group on A ring have optimal binding affinity that is at least 10 folds higher than those with fluoro or hydroxyl substituent. (Bohl C. E., Chang C., Mohler M. L., Chen J., Miller D. D., Swaan P. W., Dalton J. T. A ligand-based approach to identify quantitative structure-activity relationships for the androgen receptor. *J Med Chem.,* 47: 3765-3776,2004.) If the inventive compounds of FIGS. 7, 8 and 8A adopt the orientation mentioned above, they should not exert better binding affinity than flutamide because they do not have cyano or nitro substituent and this orientation would also abolish the potential hydrogen bond interaction with Asp 705.

Agonist and Antagonist Activity

Figure 9:
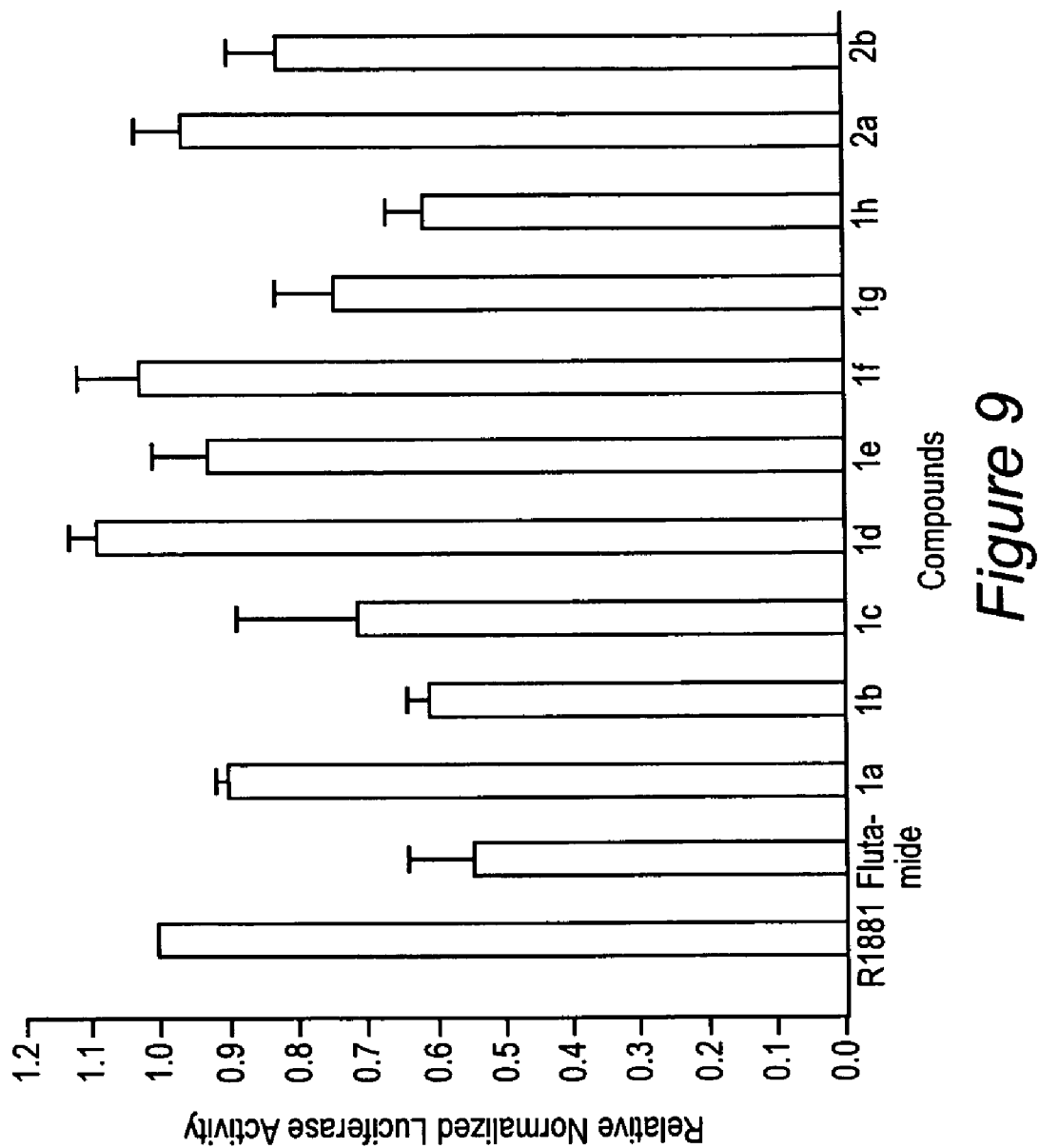
FIG. 9. Graph for data from Transient transfection reporter assay in HepG2 cells. AR antagonistic effect was determined by the ARE-driven transactivation luciferase activity in the presence of 1 nM R1881. The relative luciferase activity was quantified as RLA of 5 μM tested compound/RLA of 1 nM R1881. The RLA was mean of at least three individual tests.

To determine the agonist and antagonist activity of these compounds, the transient transfection reporter assay in HepG2 cells were employed. Generally, HepG2 cells were transfected with three plasmids by using Superfect transfection kit (Qiagen, Valencia, Calif.) including hAR expression plasmid pcDNA-hAR, a luciferase reporter plasmid containing androgen receptor response element pGL3-ARE-E4, and a normalization control, β galactosidase reporter plasmid pCMVβ. DMSO for androgenic activity and flutamide for antiandrogenic activity as the standard reference were used for comparison of androgenic and antiandrogenic effects of compounds 1a to 2b. Essentially, compounds 1a to 2b did not exert obvious androgenic effects compared with DMSO and R1881. The antiandrogenic activity of compounds 1a to 2b is shown; compound 1b and 1h exerted optimal antiandrogenic activity against R1881, and its activity is slightly less than flutamide's. (FIG. 9) For the rest, compound 1c and 1g act as weak antiandrogens. These results show that enhancement of antiandrogenic activity could be achieved by substituting the polar hydrophilic and hydrophobic groups in the D ring to increase more hydrophilic or hydrophobic interaction within compounds and helix 7 and 11 of AR ligand binding pocket. Apart from the testing against wild type hAR, because hAR mutation is one of the important factors for antiandrogen-resistant symptoms discovered in advance prostate cancer patients, we also employed transient transfection reporter assay in the prostate cancer cell line, LNCaP cells expressing a novel mutant hART877A. (McDonald S., Brive L., Agus D. B., Scher H. I., Ely K. R. Ligand responsiveness in human prostate cancer: structural analysis of mutant androgen receptors from LNCaP and CWR22 tumors. *Cancer Res.*, 60: 2317-2322, 2000.) Several antiandrogens and hormones have been reported to exert agonistic effects against mutant hART877A that was discovered in hydroxyflutamide-resistant prostate cancer patients but they showed either antagonistic or null activity against wild type AR. Compound 1b and 1h showed moderate antagonistic but no agonistic effects against wild type hAR. In results not shown here, R1881 is still able to exert significant agonism activity against mutant hART877A but compound 1b and 1h did not show obvious agonistic effects compared with vehicle, DMSO. From the above studies, compounds 1b and 1h were identified as the optimal antiandrogens.

Binding Mode

Further modeling studies with compound 1b and 1h was performed using InsightII docking program to study the potential binding mode of compound 1b and 1h.

In this model, lack of the hydrogen bond donor group on the A ring of compound 1b precludes compound 1b from interacting with Arg 752 of AR like other novel antiandrogens.

Importantly, the hydroxylmethyl group on the 3 position of compound 1b may interact with the backbone of Leu 704 and the side chain of Asn 705 by hydrogen bond interaction and can mimic the hydroxyl group of hydroxyflutamide. This hydrogen bond interaction strongly compensates for the lack of hydrogen bond donor group binding with Arg 752. Apart from this hydrogen bond interaction, the dimethyl-substituted D ring of compound 1b is able to insert a small hydrophobic pocket formed by the residues, Leu 873, Phe 876, Ile 899, and Thr 877 and contribute more binding affinity by hydrophobic interaction.

For compound 1h, a hydroxyl group is less favorable to bind to AR as the A ring of hydroxyflutamide than a hydrogen bond acceptor group like nitro and cyno groups but should be a favorable group to interact with Thr 877. Especially, except terminal hydroxyl group, compound 1h also contains fluoro groups that can interact well with Thr 877. The importance of the hydroxylmethyl group on the 3 position of compound 1h was further demonstrated by synthesizing a compound with similar structure but lacking this moiety. This modified compound did not show significant antiandrogenic effects (RLA=98%) and also exert much less binding affinity to AR than compound 1h.

FXR Evaluation

Figure 10:
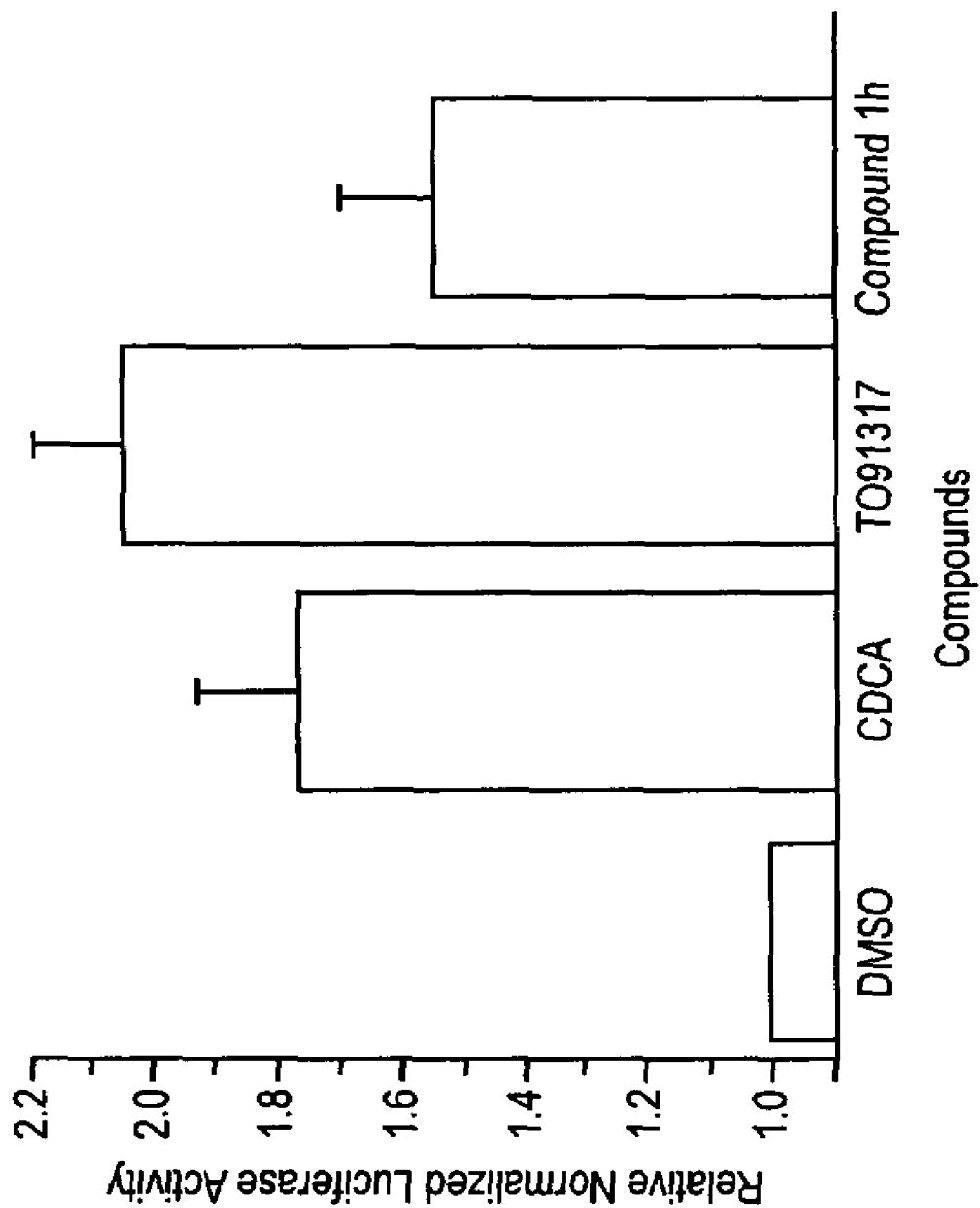
FIG. 10. Graph for data from Mammalian one hybrid assay of ligand-mediated trasnactivation of FXR in HepG2 cells. FXR agonistic effect was determined by GAL4/FXR LBD-driven transactivation luciferase activity. The relative luciferase activity was quantified as RLA of 10 μM tested compound/RLA of DMSO. The RLA was mean of at least three individual tests.
Figure 11:
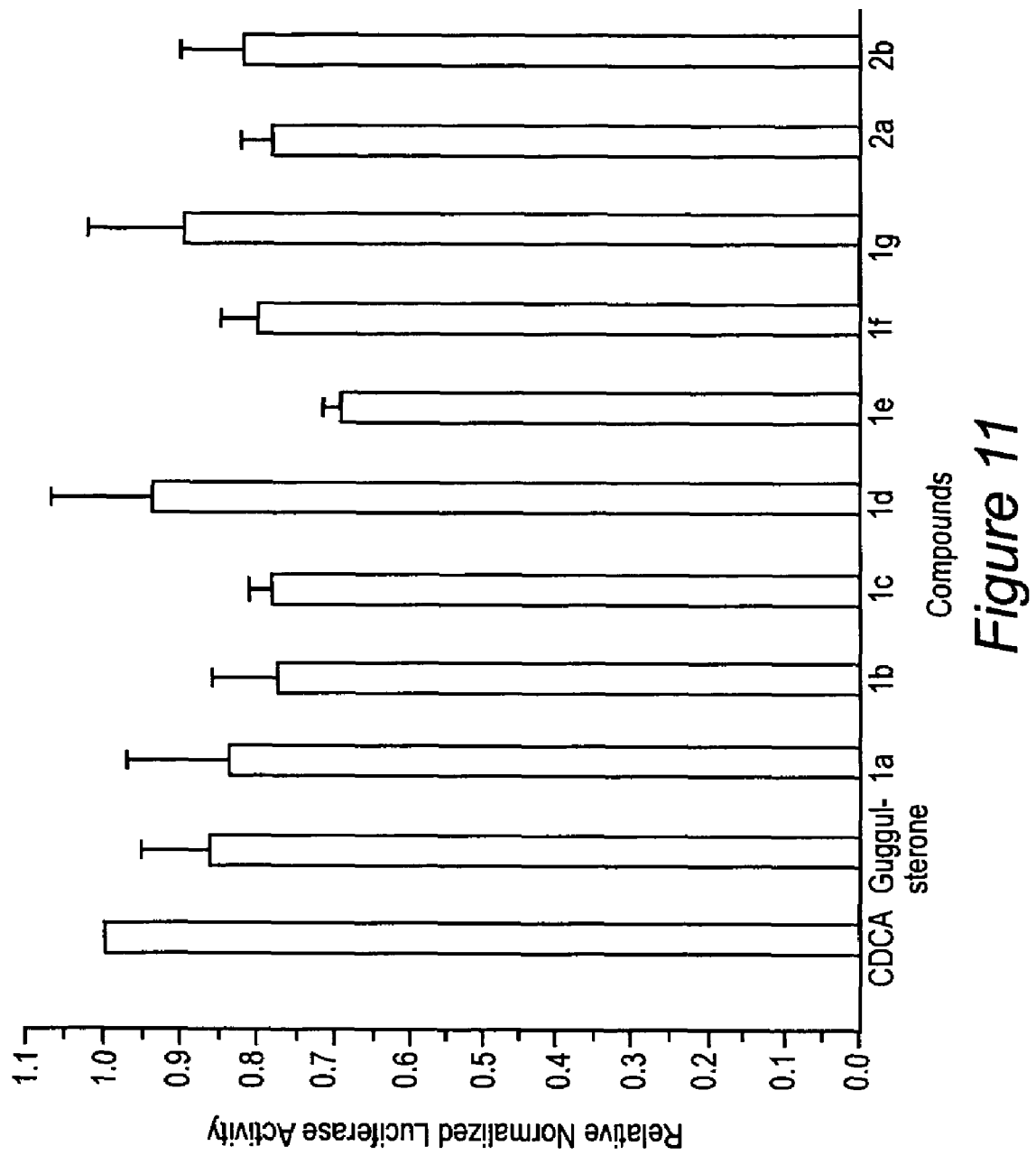
FIG. 11. Graph for data from Mammalian one hybrid assay of ligand-mediated transactivation of FXR in HepG2 cells. FXR antagonistic effect was determined by GAL4/FXR LBD-driven transactivation luciferase activity in the presence of 10 μM CDCA.

FXR is another member of nuclear receptor superfamily and its native ligands, bile acids have steroidal skeleton but contain long side chain at 17 position of steroid-like core scaffold. Based on survey of the crystal structure of FXR LBD and molecular modeling docking, the inventive compounds of FIGS. 7, 8, 8A were classified that they might also be able to interact with FXR. Additionally, recently, a novel liver x receptor (LXR) agonist, TO91317, was reported to be able to serve as FXR agonist and inventive compound 1h contains similar structural moiety as TO91317. (Houck K. A., Borchert K. M., Hepler C. D., Thomas J. S., Bramlett K. S., Michael L. F., Burris T. P. T0901317 is a dual LXR/FXR agonist. *Mol. Genet. Metab.*, 83:184-187,2004.) Therefore the inventive compounds were tested for activity against FXR. To determine the agonist and antagonist activity of these compounds against FXR, the transient transfection reporter assay in HepG2 cells was employed. In HepG2 cells, they were transfected with three plasmids including hFXR LBD expression plasmid pGal-hFXR LBD that is generated by subcloning the cDNA of hFXR LBD, produced by PCR method, into pCMV-BD and fusing the hFXR LBD to the C terminus of Gal4 DNA binding domain, a luciferase reporter plasmid containing repeated Gal4 response element pG5-Luc, and a normalization control, β galactosidase reporter plasmid pCMVβ. CDCA for agonist and guggulsterone, a novel FXR antagonist, for antagonist activity as the standard reference were used for comparison. (Urizar N. L., Liverman A. B., Dodds D. T., Silva F. V., Ordentlich P., Yan Y., Gonzalez F. J., Heyman R. A., Mangelsdorf D. J., Moore D. D. A natural product that lowers cholesterol as an antagonist ligand for FXR. *Science*, 296:1703-1706,2002.) Most tested compounds did not exert obvious agonist effect against FXR, and only compound 1h showed moderate agonist activity as shown in FIG. 10, whose activity is moderately less than CDCA and TO91317 at 10 µM. In FIG. 11, the antagonist activity of these compounds as shown, at 10 µM, most tested compounds exerted similar antagonist activity as guggulsterone and compound 1e is the most potent antagonist among them. In the crystal structure of rat FXR LBD complexed with CDCA, it reveals there are three main hydrogen bond interactions within them: (1) the 3 α hydroxyl group of CDCA oriented toward to helix 12 of FXR LBD and contacted with His 444 and Trp 466 and it can act as either hydrogen bond donor or acceptor to interact with FXR; (2) the 7 α: hydroxyl group interacted with Y366; (3) the 24 carboxyl group served as a hydrogen bond acceptor for Arg 328. (Mi L. Z., Deverakonda S., Harp J. M., Han Q., Pelliciari R., Wilson T. M., Khorasanizadeh S., Rastinejad F. Structural basis for bile acid binding and activation of the nuclear receptor FXR. *Mol. Cell*, 11: 1093-1100, 2003.) Apart from these residues, most residues in the ligand pocket of FXR pointed toward to ligand are hydrophobic. The results from the studies of structure-activity relationship of CDCA derivatives demonstrated that the 3α hydroxyl group and 24 carboxyl group of CDCA play essential roles in the agonist effects and, 3β, 7β, as well as 12 β hydroxyl substituents on CDCA are not critical for the FXR activation. (Fujino T., Une M., Imanaka T., Inoue K., Nishimaki-Mogami T. Structure-activity relationship of bile acids and bile acid analogs in regard to FXR activation. *J. Lipid Res.*, 45: 132-138, 2004.) The hypothetic binding mode of the inventive compounds in this Experimentation (FIGS. 7-11) might have two possible orientations: (1) the D ring leans toward to helix 11; (2) the D ring leans toward to helix 5. Because compounds 1a to 2b, except 1h, did not show any obvious agonist effects, they might bind to FXR LBD by leaning their D ring to helix 11 and their substituents on D ring may contact with FXR LBD through hydrophobic or hydrogen bond interaction. In this orientation, the 3-hydroxylethyl group on the core scaffold might mimic the 12β hydroxyl group of CDCA which has been shown to diminish the effects of FXR activation, but enhance the compound's binding affinity to FXR to allow them acting as competitive inhibitor for FXR. A similar condition might be seen in guggulsterone. Guggulsterone is an Indian plant resin extract and it contains 3, 15 dicarbonyl ketone functional group. However, guggulsterone only can competitively inhibit CDCA driven FXR activation but not be able to activate FXR. This agonistic deficiency should result from its lacking 24 hydrogen bond interaction with FXR LBD. On the contrary, compound 1h that contains similar moiety as T0901317, a mixed FXR and liver x receptor (LXR) agonist, might adopt different binding mode due to its unique agonist effects among this type of derivative. T0901317 lacks A ring substituents but it still can activate FXR. Similarly, compound 1h has similar structural moieties as T091317 and also acts as a FXR agonist. They may bind to FXR in the sane manner. T0901317 is also a liver x receptor (LXR) agonist and it has no hydrogen bond interaction with Glu 267 and Arg 305 as LXR natural ligand, like 22R, hydroxyl cholesterol does. (Williams S., Bledsoe R. K., Collins J. L., Boggs S., Lambert M. H., Miller A. B., Moore J., McKee D. D., Nichols J., Parks D., Watson M., Wisely B., Willson T. M. X-ray crystal structure of the liver x receptor β ligand binding domain. *J. Biol. Chem.*, 278: 27138-27143, 2003.) T0901317 binds to LXRβ LBD by leaning its hydrophilic group toward to the helix 11 and its terminal hydroxyl group contact with His 421 by hydrogen bond interaction. Although the structure-activity relationship studies of CDCA derivatives demonstrated that 24 carboxylate group is very critical for their FXR activation activities, the replacement of this 24 carboxylate moiety to hydroxyl group still can activate FXR dependent reporter transactivation in cells but is not able to enhance the association of coactivator peptide with FXR in in vitro assays. These results lead to the conclusion that the hydrogen bond interaction with Arg 328 is the main structural requirement for potent FXR agonists. However, some weak FXR agonists still can activate FXR at µM level without this moiety.

Antagonist Effects Against AR and FXR Action.

The above experimentation (FIGS. 7-11) indicates that the tetrahydroisoquinoline-N-phenylamide derivatives can exert antagonist effects against AR. Its 3-ethylhydroxyl group might play an essential role in this action.

Additionally, certain inventive compounds (see FIGS. 7-11) have been to also capable of regulating FXR action by either competing with CDCA to bind to FXR LBD or activating FXR by mimic T0901317.

The above experimentation to which FIGS. 7-11 relate is considered in the following context. Nuclear receptors including androgen receptor (AR) and farnesoid x receptor (FXR) act as transcription factors to regulate the expression of target genes involved in various diseases, including prostate cancer and x syndrome diseases. The functions of most nuclear receptors are mainly ligand-activated. Androgen, a steroid hormone and AR natural ligand, is responsible for the cellular proliferation of male sexual organs, like prostate. Currently, before this invention, treatments for prostate cancer highly rely on androgen ablation and antiandrogens. FXR modulates the transcription actions of numerous genes involved in bile acid and lipid metabolism, including phospholipid transfer protein and cholesterol 7 α hydroxylase. As a result, FXR modulators are viewed as potential treatments for bile acid and cholesterol homeostasis diseases.

In the experimentation discussed above, a lead pharmacophore was designed, based on the crystal structure of AR ligand binding domain. A series of derivatives were generated from the lead pharmacophore by synthetic methods. Their binding affinity for AR was determined by fluorescence-based competitive binding assay, and their agonistic/antagonistic activity for AR and FXR was evaluated by transient transfection reporter assays in HepG2 cells. Additionally, InsightII docking program was used to build the hypothetic binding models. Tested compounds including HRL-AR-1b (RBA=6.4) and HRL-AR-1h (RBA=12.6), showed higher binding affinity than flutamide (RBA=1). HRL-AR-1b and HRL-AR-1h exerted the most optimal antagonistic activity, consistent with their binding affinity; their anti-androgenic activity is similar to flutamide's. Additionally, these derivatives were demonstrated to act as weak antagonists for FXR except HRL-AR-1h, which behaved as a FXR agonist. Thus, potent anti-androgens and FXR modulators may be provided using compounds according to the present invention.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A compound of formula wherein
- Z is selected from the group consisting of CO, $CH_2$, and $CO(CH_2)n$, where n=1 or 2;
- R1, R2, R3, R4, R5, R6, R7, R8 and R9 are the same or different, and are selected from the group consisting of H, OH, halogens, R and OR, where R is a substituted or unsubstituted alkyl group having 1-4 carbons;
- Y is selected from the group consisting of —$CH_2$—O—R10 and —$CH_2$—NH—R10; and
- R10 is selected from the group consisting of:
  a) —$(CH_2)n$-C(=O)—N—R11, R12, where n=1-10 and R11 and R12 are the same or different, and are selected from the group consisting of substituted and unsubstituted $C_1$-$C_9$ alkyl, substituted and unsubstituted cycloalkyl, and substituted and unsubstituted aryl;
  b) —$(CH_2)n$-S(=O)—N—R11, R12, where n=1-10 and R11 and R12 are the same or different, and are selected from the group consisting of substituted and unsubstituted $C_1$-$C_9$ alkyl, substituted and unsubstituted cycloalkyl, and substituted and unsubstituted aryl;
  c) —$(CH_2)n$-$SO_2$—N—R11, R12, where n=1-10 and R11 and R12 are the same or different, and are selected from the group consisting of substituted and unsubstituted $C_1$-$C_9$ alkyl, substituted and unsubstituted cycloalkyl, and substituted and unsubstituted aryl;
  d) —$(CH_2)n$-S(=O)—R11, where n=1-10 and R11 is selected from: substituted and unsubstituted $C_1$-$C_9$ alkyl, substituted and unsubstituted cycloalkyl, and substituted and unsubstituted aryl; and
  e) —$(CH_2)n$-$SO_2$—R11, where n=1-10 and R11 is selected from the group consisting of substituted and unsubstituted $C_1$-$C_9$ alkyl, substituted and unsubstituted cycloalkyl, and substituted and unsubstituted aryl.

2. The compound of claim 1 wherein said substituted and unsubstituted $C_1$-$C_9$ alkyl is —$CH_2CH_2CH_2CF_2CF_3$.

3. The compound of claim 1 wherein R1, R2, R3, R4, R5, R6, R7, R8 and R9 are selected from the group consisting of F, $OCH_3$, OH, $CH_3$ and Cl.

4. A compound as recited in claim 1 having formula:

5. A compound as recited in claim 1 having formula:

6. A compound as recited in claim 1 having formula:

7. A compound as recited in claim 1 having formula:

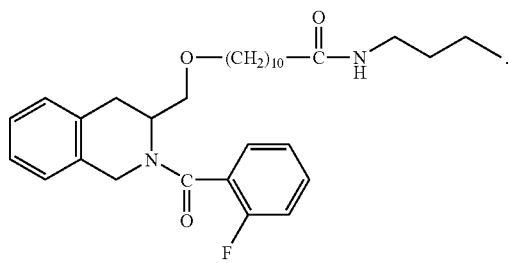

8. A compound as recited in claim 1 having formula:

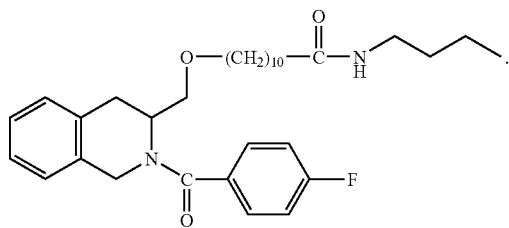

9. A compound as recited in claim 1 having formula:

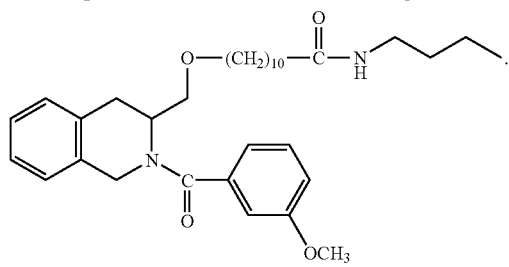

10. A compound as recited in claim 1 having formula:

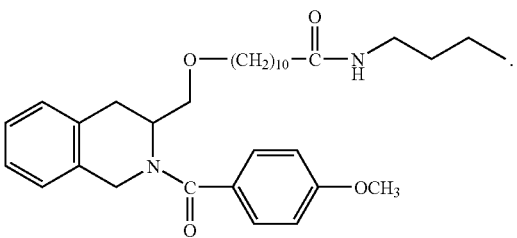

11. A compound as recited in claim 1 having formula:

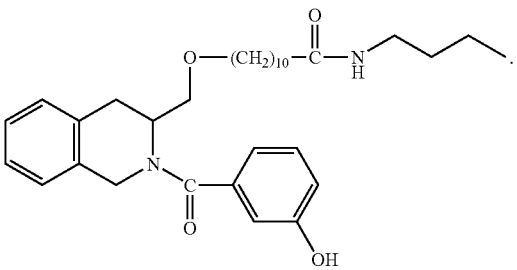

12. A compound as recited in claim 1 having formula:

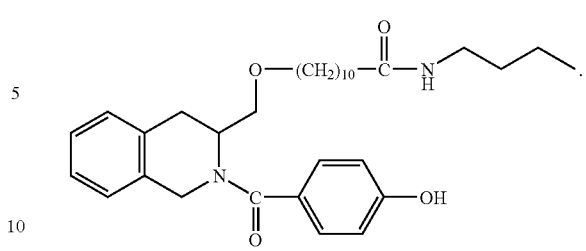

13. A compound as recited in claim 1 having formula:

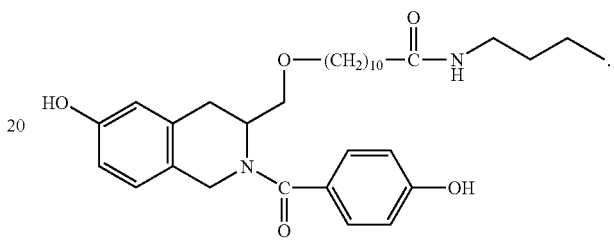

14. A compound as recited in claim 1 having formula:

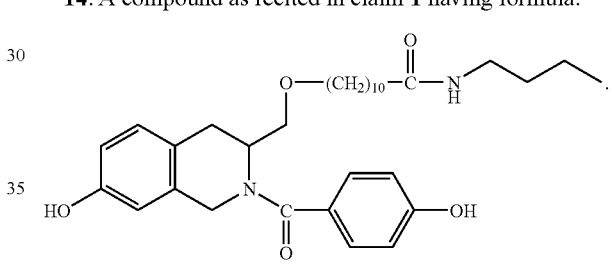

15. A compound as recited in claim 1 having formula:

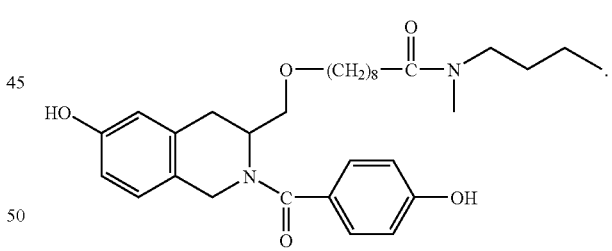

16. A compound as recited in claim 1 having formula:

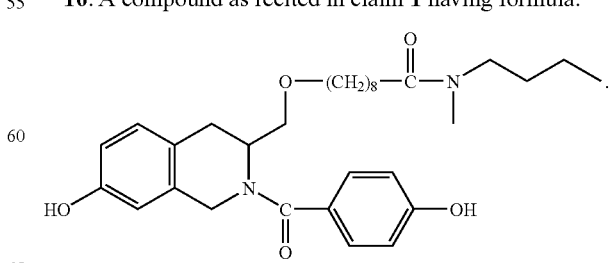

17. A compound as recited in claim 1 having formula:

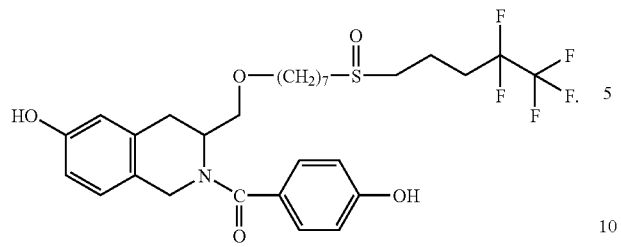

18. A compound as recited in claim 1 having formula:

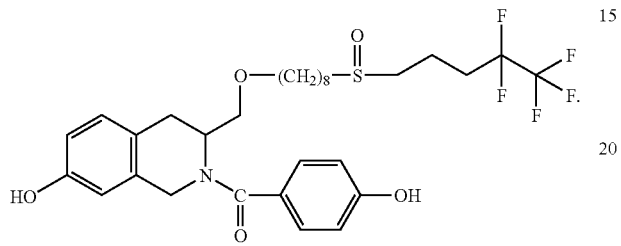

19. A compound as recited in claim 1 having formula:

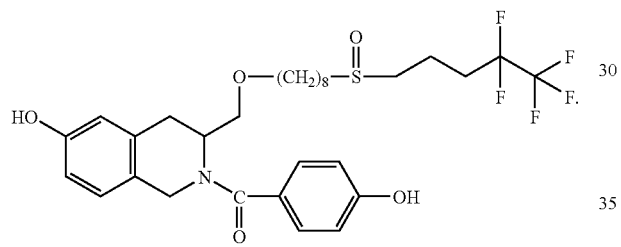

20. A compound as recited in claim 1 having formula:

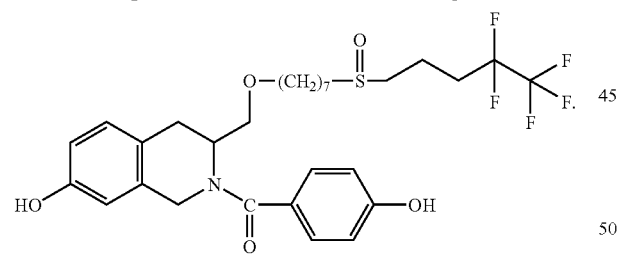

21. A compound as recited in claim 1 having formula:

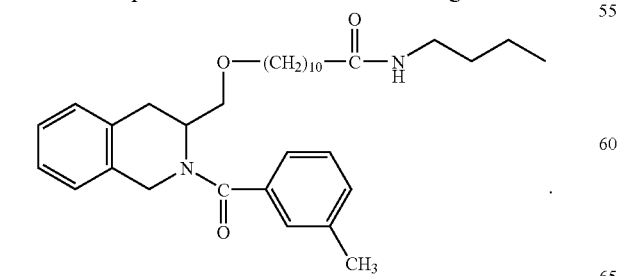

22. A compound as recited in claim 1 having formula:

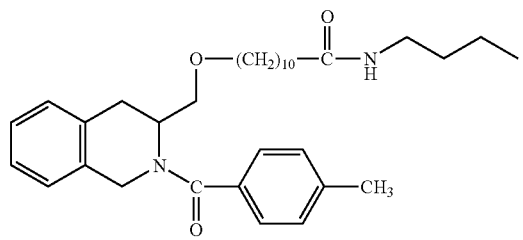

23. A compound as recited in claim 1 having formula:

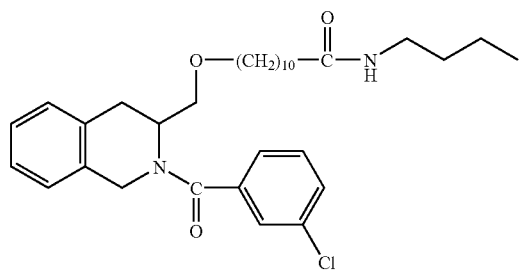

24. A compound as recited in claim 1 having formula:

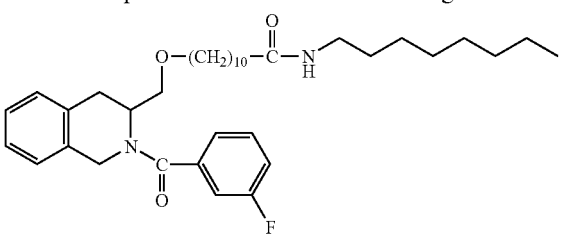

25. A compound as recited in claim 1 having formula:

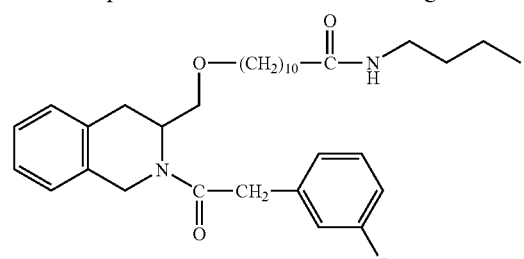

26. A method for treating breast cancer tumors in a patient in need thereof, comprising the step of
administering to said patient a compound of generic formula

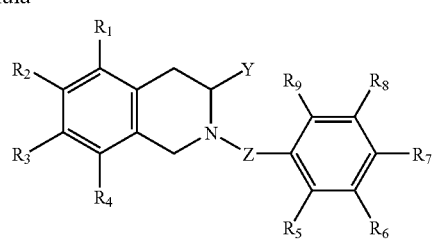

wherein
Z is selected from the group consisting of CO, CH$_2$, and CO(CH$_2$)n, where n=1 or 2;

R1, R2, R3, R4, R5, R6, R7, R8 and R9 are the same or different, and are selected from the group consisting of H, OH, halogens, R and OR, where R is a substituted or unsubstituted alkyl group having 1-4 carbons;

Y is selected from the group consisting of —CH$_2$—O—R10 and —CH$_2$—NH—R10; and R10 is selected from the group consisting of:
- a) —(CH$_2$)n-C(=O)—N—R11, R12, where n=1-10 and R11 and R12 are the same or different, and are selected from the group consisting of substituted and unsubstituted C$_1$-C$_9$ alkyl, substituted and unsubstituted cycloalkyl, and substituted and unsubstituted aryl;
- b) —(CH$_2$)n-S(=O)—N—R11, R12, where n=1-10 and R11 and R12 are the same or different, and are selected from the group consisting of substituted and unsubstituted C$_1$-C$_9$ alkyl, substituted and unsubstituted cycloalkyl, and substituted and unsubstituted aryl;
- c) —(CH$_2$)n-SO$_2$—N—R11, R12, where n=1-10 and R11 and R12 are the sane or different, and are selected from the group consisting of substituted and unsubstituted C$_1$-C$_9$ alkyl, substituted and unsubstituted cycloalkyl, and substituted and unsubstituted aryl;
- d) —(CH$_2$)n-S(=O)—R11, where n=1-10 and R11 is selected from: substituted and unsubstituted C$_1$-C$_9$ alkyl, substituted and unsubstituted cycloalkyl, and substituted and unsubstituted aryl; and
- e) —(CH$_2$)n-SO$_2$—R11, where n=1-10 and R11 is selected from the group consisting of substituted and unsubstituted C$_1$-C$_9$ alkyl, substituted and unsubstituted cycloalkyl, and substituted and unsubstituted aryl.

\* \* \* \* \*

SEQUENCE LISTING

```
<160> NUMBER OF SEQ ID NOS: 10

<210> SEQ ID NO 1
<211> LENGTH: 27
<212> TYPE: DNA
<213> ORGANISM: Artificial
<220> FEATURE:
<223> OTHER INFORMATION: synthetic oligonucleotide primer

<400> SEQUENCE: 1
ggatccatga ccatgaccct ccacacc                                        27

<210> SEQ ID NO 2
<211> LENGTH: 27
<212> TYPE: DNA
<213> ORGANISM: Artificial
<220> FEATURE:
```

```
<223> OTHER INFORMATION: synthetic oligonucleotide primer

<400> SEQUENCE: 2
gtcgactcag actgtggcag gaaaccc                                        27

<210> SEQ ID NO 3
<211> LENGTH: 29
<212> TYPE: DNA
<213> ORGANISM: Artificial
<220> FEATURE:
<223> OTHER INFORMATION: synthetic oligonucleotide primer

<400> SEQUENCE: 3
ggatccatgg atataaaaaa ctcaccatc                                      29

<210> SEQ ID NO 4
<211> LENGTH: 28
<212> TYPE: DNA
<213> ORGANISM: Artificial
<220> FEATURE:
<223> OTHER INFORMATION: synthetic oligonucleotide primer

<400> SEQUENCE: 4
gtcgactcac tgagactgtg ggttctgg                                       28

<210> SEQ ID NO 5
<211> LENGTH: 24
<212> TYPE: DNA
<213> ORGANISM: Artificial
<220> FEATURE:
<223> OTHER INFORMATION: synthetic oligonucleotide primer

<400> SEQUENCE: 5
catatgacca tgaccctcca cacc                                           24

<210> SEQ ID NO 6
<211> LENGTH: 28
<212> TYPE: DNA
<213> ORGANISM: Artificial
<220> FEATURE:
<223> OTHER INFORMATION: synthetic oligonucleotide primer

<400> SEQUENCE: 6
ggatcctcag actgtggcag ggaaaccc                                       28

<210> SEQ ID NO 7
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 7
ctcgagtggt ttttgacccc gaacg                                          25

<210> SEQ ID NO 8
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 8
ctcgagcccg gggtctagaa gatcc                                          25
```

```
<210> SEQ ID NO 9
<211> LENGTH: 39
<212> TYPE: DNA
<213> ORGANISM: Artificial
<220> FEATURE:
<223> OTHER INFORMATION: synthetic oligonucleotide primer

<400> SEQUENCE: 9
ggcttactga ccaacctggc atacagggag ctggttcac                              39

<210> SEQ ID NO 10
<211> LENGTH: 39
<212> TYPE: DNA
<213> ORGANISM: Artificial
<220> FEATURE:
<223> OTHER INFORMATION: synthetic oligonucleotide primer

<400> SEQUENCE: 10
gtgaaccagc tccctgtatg ccaggttggt cagtaagcc                              39
```